(12) United States Patent
Goswami et al.

(10) Patent No.: US 6,376,163 B1
(45) Date of Patent: Apr. 23, 2002

(54) PHOTOBLEACHABLE COMPOSITION, PHOTOGRAPHIC ELEMENT CONTAINING THE COMPOSITION AND PHOTOBLEACHABLE METHOD

(75) Inventors: Ramanuj Goswami, Webster; Samir Y. Farid, Rochester; Robert J. Perry, Niskayuna; Paul A. Zielinski, Rochester, all of NY (US); Ian R. Gould, Phoenix, AZ (US); Kevin W. Williams, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/510,002

(22) Filed: Feb. 22, 2000

(51) Int. Cl.⁷ .............................. G03C 1/73; G03C 1/83
(52) U.S. Cl. ...................... 430/559; 430/510; 430/517
(58) Field of Search ................................ 430/559, 510, 430/517

(56) References Cited

U.S. PATENT DOCUMENTS

| | | | |
|---|---|---|---|
| 3,615,432 A | 10/1971 | Jenkins et al. | 430/2 |
| 3,745,009 A | 7/1973 | Jenkins et al. | 430/522 |
| 3,988,156 A * | 10/1976 | Sturmer | 430/522 |
| 4,075,017 A | 2/1978 | Goffe et al. | 430/353 |
| 4,111,699 A * | 9/1978 | Krueger | 430/522 |
| 4,548,896 A | 10/1985 | Sabongi et al. | 430/332 |
| 4,581,323 A | 4/1986 | Fisher et al. | 430/513 |
| 4,701,402 A | 10/1987 | Patel et al. | 430/332 |
| 4,743,528 A | 5/1988 | Farid et al. | 430/281 |
| 4,743,529 A | 5/1988 | Farid et al. | 430/281 |
| 4,743,530 A | 5/1988 | Farid et al. | 430/281 |
| 4,743,531 A | 5/1988 | Farid et al. | 430/281 |
| 4,769,459 A | 9/1988 | Patel et al. | 544/301 |
| 4,875,080 A | 10/1989 | Kimura et al. | 355/246 |
| 5,312,721 A | 5/1994 | Gesing | 430/449 |

FOREIGN PATENT DOCUMENTS

| | | |
|---|---|---|
| EP | 0 308 274 | 8/1994 |
| GB | 2 083 832 A | 3/1982 |
| WO | WO 93/04411 | 3/1993 |

\* cited by examiner

*Primary Examiner*—Hoa Van Le
(74) *Attorney, Agent, or Firm*—Edith A. Rice

(57) ABSTRACT

A UV or visible-light sensitive photobleachable dye composition substantially free of polymerizable monomer comprising a photobleachable dye and an N-oxyazinium compound, a photographic element containing such a photobleachable composition, and a method for bleaching a photographic element.

9 Claims, No Drawings

PHOTOBLEACHABLE COMPOSITION, PHOTOGRAPHIC ELEMENT CONTAINING THE COMPOSITION AND PHOTOBLEACHABLE METHOD

FIELD OF THE INVENTION

This invention relates to a photobleachable dye composition. The present invention also relates to an imaging element containing the composition, and a method for photobleaching of a photographic element containing the composition.

BACKGROUND OF THE INVENTION

In the field of photography, it is known to provide photographic elements comprising filter or antihalation compositions to improve the resolution of photographic materials. These antihalation dye compositions can be in the emulsion layer, or preferably in a non-image forming auxiliary layer. Without these antihalation dye layers, radiation reaching the photographic emulsion layer would be reflected, and image sharpness would decrease. After the image-wise exposure of the photographic element, the antihalation dye composition is generally bleached during or after the processing. Thermally bleachable antihalation dye compositions are known. Photobleachable antihalation dye compositions and chemically bleachable antihalation dye compositions are also known wherein subsequent to the imaging and processing steps, the film could then be exposed to a suitable light source or chemicals to bleach the dye.

For example, U.S. Pat. No. 4,548,896 discloses an image-wise bleachable composition comprising a dye in reactive association with a mesoionic compound, the composition being bleached through exposure to radiation at a wavelengths between 200 and 1000 nm.

U.S. Pat. No. 3,745,009 discloses a bleachable dye wherein an N-oxy substituent is part of the dye chromophore. The synthesis of these dyes is usually complex. Further, these dyes need to be carefully handled. Due to their inherent bleachable ability, they are not light stable.

U.S. Pat. Nos. 4,743,528, 4,743,529, 4,743,530 and 4,743,531 disclose a polymerisable composition comprising an azinium activator, a photosensitizer, and an ethylenically unsaturated monomers.

EP 308274 discloses a photobleachable cyanine dye composition containing a borate salt. The technology appears to be useful with a very limited variety of bleachable dyes.

Many of the known bleaching methods suffer from one or more disadvantages. They are limited to either heat or light sensitivity or to the required numbers of steps for carrying out the bleaching. Some methods are also limited to the narrow number of useful dyes, or by the effort required for synthesizing the useful dye.

SUMMARY OF THE INVENTION

It is desirable to find a photobleachable composition that eliminates the drawbacks of the known photobleachable compositions.

It is also desirable to provide a photographic element containing a photobleachable composition and a method for bleaching the photographic element containing the photobleachable composition.

These and other objects are achieved by the present invention, which provides a visible-light sensitive photobleachable dye composition, substantially free of polymerisable monomer, comprising a photobleachable dye and an N-oxyazinium compound.

The invention also relates to an imaging element comprising a support having thereon at least one image forming layer, and at least one non-image forming layer wherein the element further comprises a visible-light sensitive photobleachable composition containing a photobleachable dye and an N-oxyazinium compound.

Then, the invention relates to a method for bleaching a photographic element comprising a support having thereon at least one image forming layer, at least one non-image forming layer comprising a visible-light sensitive photobleachable composition containing a photobleachable dye and an N-oxyazinium compound, the method comprising:

exposing and processing the photographic element, and exposing the exposed and processed element, to radiation that can be absorbed either by the photobleachable dye or by the N-oxyazinium compound.

The method involves photochemically bleaching the photobleachable dyes relying on photoreactions of the photobleachable dye with an N-oxyazinium compound.

This invention provides a photobleaching method that can be advantageously carried out for a wide variety of photobleachable dyes such as sensitizing dyes, filter dyes, image dyes, infrared dyes or antihalation dyes. In addition, in the present invention, the photobleachable dye and the N-oxyazinium are distinct entities. As a result, the dyes can be easily handled in light, since the bleaching effect occurs only in the presence of the N-oxyazinium.

DETAILED DESCRIPTION OF THE INVENTION

When reference in this application is made to a particular group, unless otherwise specifically stated, the group may itself be unsubstituted or substituted with one or more substituents (up to the maximum possible number). For example, "alkyl" group refers to a substituted or unsubstituted alkyl group, such as aralkyl group or sulfoalkyl group while "aryl" group refers to a substituted or unsubstituted aryl group (with up to six substituents) such as alkaryl or sulfoaryl group. The substituent may be itself substituted or unsubstituted.

Generally, unless otherwise specifically stated, substituents include any substituents, whether substituted or unsubstituted, which do not destroy properties necessary for the photographic utility. Examples of substituents include known substituents, such as: halogen, for example, chloro, fluoro, bromo, iodo; alkoxy, particularly those "lower alkyl" (that is, with 1 to 6 carbon atoms, for example, methoxy, ethoxy; substituted or unsubstituted alkyl, particularly lower alkyl (for example, methyl, trifluoromethyl); thioalkyl (for example, methylthio or ethylthio), particularly either of those with 1 to 6 carbon atoms; substituted and unsubstituted aryl, particularly those having from 6 to 20 carbon atoms (for example, phenyl); and substituted or unsubstituted heteroaryl, particularly those having a 5 or 6-membered ring containing 1 to 3 heteroatoms selected from N, O, or S (for example, pyridyl, thienyl, furyl, pyrrolyl); acid or acid salt groups such as any of those described below; and others known in the art. Alkyl substituents may specifically include "lower alkyl" (that is, having 1–6 carbon atoms), for example, methyl, ethyl, and the like. Further, with regard to any alkyl group or alkylene group, it will be understood that these can be branched or unbranched and include ring structures.

In the scope of the invention, the N-oxyazinium compound is an N-oxy-N-heterocyclic compound having a heterocyclic nucleus, such as a pyridinium, diazinium, or triazinium nucleus. The N-oxyazinium compound can include one or more aromatic rings, typically carbocyclic aromatic rings, fused with the N-oxy-N-heterocyclic compound, including quinolinium, isoquinolinium, benzodiazinium, phenanthridium and naphthodiazinium. Any convenient charge balancing counter-ion can be employed to complete the N-oxyazinium compounds. The oxy group (—O—$R_1$) of the N-oxyazinium compound which quaternizes the ring nitrogen atom of the azinium nucleus can be selected from among a variety of synthetically convenient oxy groups. The group $R_1$ can, for example, be an alkyl group such as methyl, ethyl, butyl, benzyl, an aralkyl group (e.g., benzyl or phenethyl) and a sulfoalkyl group (e.g., sulfomethyl). The group $R_1$ can be an aryl group such as a phenyl group. In another form $R_1$ can be an acyl group, such as an —C(O)—$R_3$ group, where $R_3$ is an alkyl and aryl groups such as phenyl or naphthyl, tolyl, xylyl, etc. When $R_1$ is an alkyl group, it typically contains from 1 to 18 carbon atoms, when $R_1$ is an aryl group, it typically contains from 6 to 18 carbon atoms.

Illustrative examples of useful N-oxyazinium compounds are shown by the formulae below:

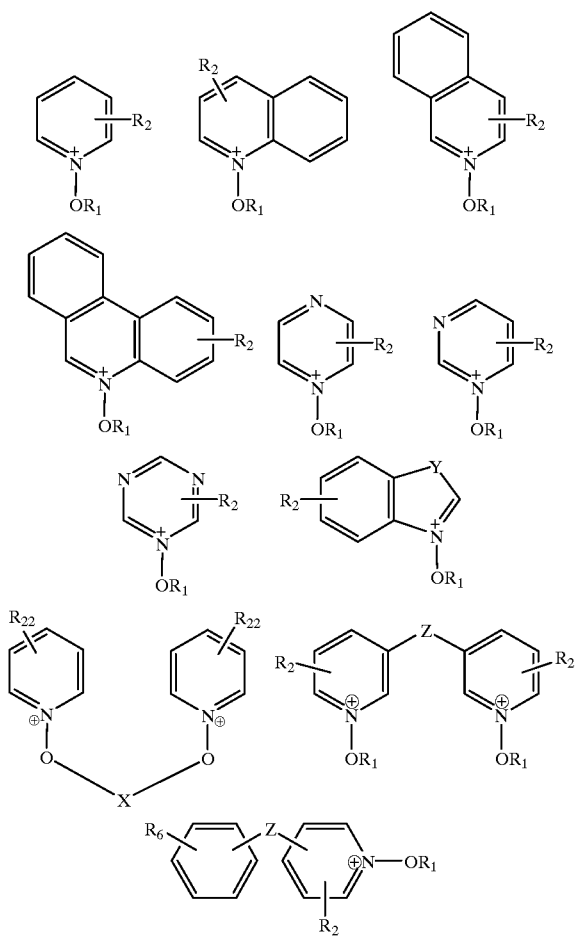

wherein $R_1$ represents alkyl group of 1–12 carbons, or alkyl group substituted with one or more groups selected from the group consisting of acyloxy, alkoxy, aryloxy, alkylthio, arylthio, alkylsulfonyl, thiocyano, cyano, halogen, alkoxycarbonyl, aryloxycarbonyl, acetyl, aroyl, alkylaminocarbonyl, arylaminicarbonyl, alkylaminocarbonyloxy, alkylaminocarbonyloxy, acylamino, carboxy, sulfo, trihalomethyl, alkyl, aryl, heteroaryl, alkylureido, arylureido, succinimido, and phthalimido substituent; aryl group, or acyl group; each $R_2$, $R_{22}$ and $R_6$ represents independently hydrogen, an alkyl group of 1–12 carbons, an aryl or heteroaryl group, unsubstituted or substituted with one or more substituents selected from the group consisting of an acyloxy, alkoxy, aryloxy, alkylthio, arylthio, alkylsulfonyl, thiocyano, cyano, halogen, alkoxycarbonyl, aryloxycarbonyl, acetyl, aroyl, alkylaminocarbonyl, arylaminicarbonyl, alkylaminocarbonyloxy, arylaminocarbonyloxy, acylamino, carboxy, sulfo, trihalomethyl, alkyl, aryl, heteroaryl, alkylureido, arylureido, succinimido and phthalimido substituent, or an acyloxy, hydroxy, alkoxy, aryloxy, alkylthio, arylthio, alkylsulfonyl, thiocyano, cyano, halogen, alkoxycarbonyl, aryloxycarbonyl, acetyl, aroyl, alkylaminocarbonyl, arylaminicarbonyl, alkylaminocarbonyloxy, arylaminocarbonyloxy, acylamino, amino, alkylamino, arylamino, carboxy, sulfo, trihalomethyl, alkyl, aryl, heteroaryl, alkylureido, arylureido, succinimido, phthalimido group, —CO—$R_3$ wherein $R_3$ is an alkyl or an aryl group, or —(CH=CH)$_m$—$R_4$ wherein $R_4$ is an aryl or heterocyclic group; m is 1 or 2; Y is selected from the group consisting of S, O, Se, —C($R_1$)$_2$, and —N$R_1$; X is a divalent linking group selected from a group consisting of substituted or unsubstituted methylenes, (—CR$_5$R$_7$—)$_n$ and [(—CR$_5$R$_7$)$_n$—X$_1$—(CR$_5$R$_7$—)$_p$] wherein $R_5$ or $R_7$ are independently hydrogen, alkyl, substituted alkyl, aryl, substituted aryl, heteroaryl, substituted heteroaryl group, n and p are from 1–12, $X_1$ is aryl or heteroaryl nuclei, carbonyl, sulfo, thio, oxy; and Z is an alkylidene group.

In the scope of the invention, each of the above formulae can comprise one or more $R_2$, $R_{22}$ or $R_6$ groups.

Useful N-oxyazinium compounds can also be represented by the following formula

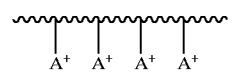

wherein A$^+$ is the N-oxyazinium moiety. The linking alkyl chain can have additional substituents, e.g., ether, ester, amide, etc.

According to one embodiment, the N-oxyazinium compound is a compound having one of the following formulae:

(II)

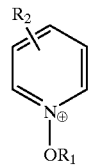

(III)

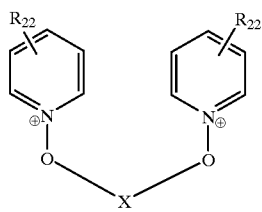

wherein $R_1$ is an alkyl, an aryl or an acyl, $R_2$ or $R_{22}$ are independently a hydrogen atom, alkyl, aryl, heterocyclic, carboxylic, carboxylate, carbonamido, sulfonamido, nitryl, groups, —CO—$R_3$ wherein $R_3$ is an alkyl group or aryl group, or —CH=CH$)_m$—$R_4$ group wherein $R_4$ is an aryl or heterocyclic group; X is an alkylene group, preferably —CH$_2)_n$— wherein n is from 1 to 12.

According to a specific embodiment, $R_1$ is preferably an alkyl having from 1 to 18 carbon atoms or an aryl group having from 6 to 18 carbon atoms.

Illustrative examples of N-oxyazinium compounds useful in the present invention are one of the following compounds:

(II)

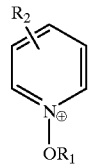

(III)

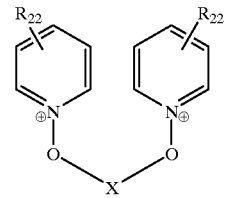

| $R_2$ or $R_{22}$ | $R_1$ or X |
|---|---|
| A-1 | $R_2$ = 4-Ph | $R_1$ = Me |
| A-2 | $R_2$ = 4-Ph | $R_1$ = (CH$_2$)$_3$—Ph |
| A-3 | $R_2$ = 4-Ph | $R_1$ = (CH$_2$)$_3$—SO$_3^-$ |
| A-4 | $R_2$ = 4-Ph | $R_1$ = 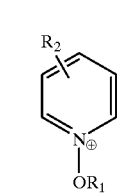 |
| A-5 | $R_2$ = 4-Ph | $R_1$ = 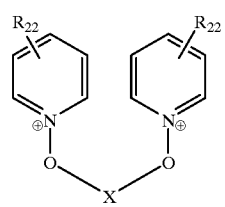 |
| A-6 | $R_2$ = 4-CN | $R_1$ = Me |
| A-7 | $R_2$ = 3-CO$_2$Me | $R_1$ = Me |
| A-8 | $R_2$ = 3-CO$_2$—(CH$_2$)$_2$—Ph | $R_1$ = Me |
| A-9 | $R_{22}$ = 4-Ph | X = (CH$_2$)$_3$ |

(II)

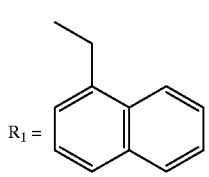

(III)

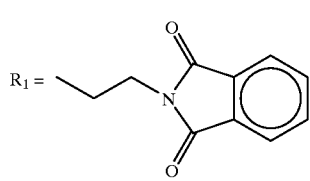

| $R_2$ or $R_{22}$ | $R_1$ or X |
|---|---|
| A-10 | $R_{22}$ = 4-Ph | X = (CH$_2$)$_4$ |
| A-11 | $R_{22}$ = 4-Ph | X = (CH$_2$)$_5$ |
| A-12 | $R_2$ = 3-Ph | $R_1$ = Me |
| A-13 | $R_2$ = 3,4-benzo | $R_1$ = Me |
| A-14 | $R_{22}$ = 3,4-benzo | X = (CH$_2$)$_3$ |
| A-15 | $R_2$ = H | $R_1$ = (CH$_2$)$_3$—SO$_3^-$ |
| A-16 | $R_2$ = H | $R_1$ = 4-nitrophenyl |
| A-17 | $R_{22}$ = H | X = (CH$_2$)$_2$ |
| A-18 | $R_{22}$ = H | X = (CH$_2$)$_3$ |
| A-19 | $R_2$ = 2-Me | $R_1$ = Me |
| A-20 | $R_2$ = 2-Me | $R_1$ = (CH$_2$)$_3$—SO$_3^-$ |
| A-21 | $R_2$ = 4-Me | $R_1$ = Me |
| A-22 | $R_{22}$ = 4-Me | X = (CH$_2$)$_4$ |
| A-23 | $R_2$ = 4-CO$_2$ | $R_1$ = Me |
| A-24 | $R_2$ = 4-CON(CH$_2$CH$_2$OH)$_2$ | $R_1$ = (CH$_2$)$_3$—SO$_3^-$ |

According to a preferred embodiment, the N-oxyazinium compound has a reduction potential less negative than −1.4 V, and comprises an N-oxy group capable of releasing an oxy radical that reacts with the photobleachable dye to produce bleached compound. In this patent application, reduction potentials are reported as "V" which represents "volts versus a saturated calomel reference electrode". Reduction potentials of N-oxyazinium compounds can be measured by standard methods well known to those of skill in the art.

The composition of the invention can contain one or more of any of the N-oxyazinium compounds disclosed therein.

The N-oxyazinium compounds are associated with a counter ion that is not involved in the activity of the present composition and can be any of the conventional anions, e.g., halide, fluoroborate, hexafluorophosphate, toluene sulfonate, etc. It can also be an oligomeric or polymeric species.

In the scope of the invention, the photobleachable dye is any dye that by reaction with an N-oxyazinium compound gives a bleached compound. According to the invention, a bleached compound is a colorless compound or a compound less colored than the dye.

The photobleachable composition is substantially free of polymerizable monomer, for example polymerizable monomer preferably is present in an amount less than 10% of the photobleachable composition, more preferable less than 5% and most preferably less than 1%.

The photobleachable dyes useful in the invention can be for example, cyanine dyes, complex cyanine dyes, merocyanine dyes, complex merocyanine dyes, homopolar cyanine dyes, styryl dyes, oxonol dyes, hemioxonol dyes, and hemicyanine dyes, squarilium dyes, coumarin dyes, rhodamine dyes, acridine dyes, oxanol dyes etc. Representative bleachable dyes are discussed in *Research Disclosure*, Item 36544, September 1996, the disclosure of which, including the disclosure of references cited therein are incorporated herein by reference. These dyes may be synthesized by those skilled in the art according to the procedures described herein or F. M. Hamer, *The Cyanine Dyes and Related Compounds* (Interscience Publishers, New York, 1964).

Photobleachable cyanine or merocyanine dyes can be represented by the general formulae D1–D5 below:

D1

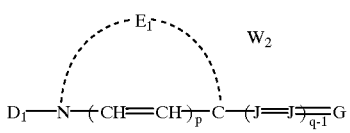

wherein:
E$_1$ and E$_2$ represent the atoms necessary to form a substituted or unsubstituted hetero ring and may be the same or different,
each J independently represents a methine group,
q is a positive integer of from 1 to 4,
p and r each independently represents 0 or 1,
D$_1$ and D$_2$ each independently represents alkyl or aryl groups, and
W$_2$ is a counterion as necessary to balance the charge;

D2

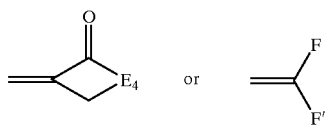

wherein E$_1$, D$_1$, J, p, q and W$_2$ are as defined above for formula D1 and G represents

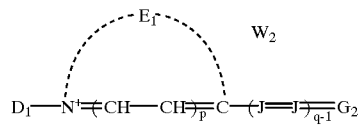

wherein E$_4$ represents the atoms necessary to complete a substituted or unsubstituted heterocyclic nucleus, and F and F$^1$ each independently represents a cyano group, an ester group, an acyl group, a carbamoyl group or an alkylsulfonyl group;

D3

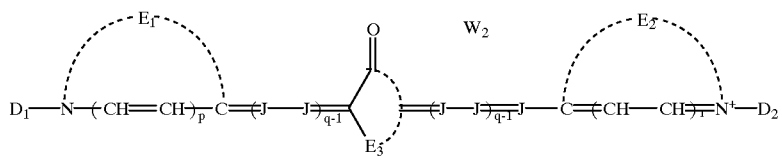

wherein D$_1$, E$_1$, J, p, q and W$_2$ are as defined above for formula D1, and G$_2$ represents an amino group or a substituted or unsubstituted aryl group;

D4

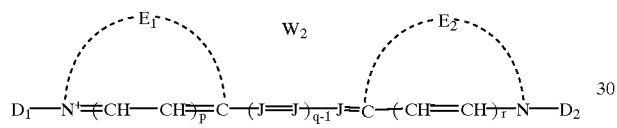

wherein D$_1$, E$_1$, D$_2$, E$_1$, J, p, q, r and W$_2$ are as defined for formula D1 above, and E$_3$ is defined the same as E$_4$ for formula D2 above;

D5 wherein D$_1$, E$_1$, J, G, p, q, r, W$_2$ and E$_3$ are as defined above.

In the above formulas, E$_1$ and E$_2$ each independently represents the atoms necessary to complete a substituted or unsubstituted 5- or 6-membered heterocyclic nucleus. These include a substituted or unsubstituted: thiazole nucleus, oxazole nucleus, selenazole nucleus, quinoline nucleus, tellurazole nucleus, pyridine nucleus, thiazoline nucleus, indoline nucleus, oxadiazole nucleus, thiadiazole nucleus, or imidazole nucleus. This nucleus may be substituted with known substituents, such as halogen (e.g., chloro, fluoro, bromo), alkoxy (e.g., methoxy, ethoxy), substituted or unsubstituted alkyl (e.g., methyl, trifluoromethyl), substituted or unsubstituted aryl, substituted or unsubstituted aralkyl, sulfonate, and others known in the art.

In one embodiment of the invention, when dyes according to formula D$_1$ are used E$_1$ and E$_2$ each independently represent the atoms necessary to complete a substituted or unsubstituted thiazole nucleus, a substituted or unsubstituted selenazole nucleus, a substituted or unsubstituted imidazole nucleus, or a substituted or unsubstituted oxazole nucleus.

Examples of useful nuclei for E$_1$ and E$_2$ include: a thiazole nucleus, e.g., thiazole, 4-methylthiazole, 4-phenylthiazole, 5-methylthiazole, 5-phenylthiazole, 4,5-dimethyl-thiazole, 4,5-diphenylthiazole, 4-(2-thienyl) thiazole, benzothiazole, 4-chlorobenzothiazole, 5-chlorobenzothiazole, 6-chlorobenzothiazole, 7-chlorobenzothiazole, 4-methylbenzothiazole, 5-methylbenzothiazole, 6-methylbenzothiazole, 5-bromobenzothiazole, 6-bromobenzothiazole, 5-phenylbenzothiazole, 6-phenylbenzothiazole, 4-methoxybenzothiazole, 5-methoxybenzothiazole, 6-methoxybenzothiazole, 4-ethoxybenzothiazole, 5-ethoxybenzothiazole, tetrahydrobenzothiazole, 5,6-dimethoxybenzothiazole, 5,6-dioxymethylbenzothiazole, 5-hydroxybenzothiazole, 6-5-dihydroxybenzothiazole, naphtho[2,1-d]thiazole, 5-ethoxynaphtho[2,3-d]thiazole, 8-methoxynaphtho[2,3-d]thiazole, 7-methoxynaphtho[2,3-d]thiazole, 4'-methoxythianaphtheno-7',6'-4,5-thiazole, etc.; an oxazole nucleus, e.g., 4-methyloxazole, 5-methyloxazole, 4-phenyloxazole, 4,5-diphenyloxazole, 4-ethyloxazole, 4,5-dimethyloxazole, 5-phenyloxazole, benzoxazole, 5-chlorobenzoxazole, 5-methylbenzoxazole, 5-phenylbenzoxazole, 6-methylbenzoxazole,, 5,6-dimethylbenzoxazole, 4,6-dimethylbenzoxazole, 5-ethoxybenzoxazole, 5-chlorobenzoxazole, 6-methoxybenzoxazole, 5-hydroxybenzoxazole, 6-hydroxybenzoxazole,, naphtho[2,1-d]oxazole, naphtho[1,2-d]oxazole, etc.; a selenazole nucleus, e.g., 4-methylselenazole, 4-phenylselenazole, benzoselenazole, 5-chlorobenzoselenazole, 5-methoxybenzoselenazole, 5-hydroxybenzoselenazole, tetrahydrobenzoselenazole, naphtho[2,1-d]selenazole, naphtho[1,2-d]selenazole, etc.; a pyridine nucleus, e.g., 2-pyridine, 5-methyl-2-pyridine, 4-pyridine, 3-methyl-4-pyridine, 3-methyl-4-pyridine, etc.; a quinoline nucleus, e.g., 2-quinoline, 3-methyl-2-quinoline, 5-ethyl-2-quinoline, 6-chloro-2-quinoline, 8-chloro-2-quinoline, 6-methoxy-2-quinoline, 8-ethoxy-2-quinoline, 8-hydroxy-2-quinoline, 4-quinoline, 6-methoxy-4-quinoline, 7-methyl-4-quinoline, 8-chloro-4-quinoline, etc.; a tellurazole nucleus, e.g., benzotellurazole, naphtho[1.2-d]benzotellurazole, 5,6-dimethoxybenzotellurazole, 5-methoxybenzotellurazole, 5-methylbenzotellurazole; a thiazoline nucleus, e.g.,thiazoline, 4-methylthiazoline, etc.; a benzimidazole nucleus, e.g., benzimidazole, 5-trifluoromethylbenzimidazole, 5,6-dichlorobenzimidazole; and indole nucleus, 3,3-dimethylindole, 3,3-diethylindole, 3,3,5-trimethylindole; or a diazole nucleus, e.g., 5-phenyl-1,3,4-oxadiazole, 5-methyl-1,3,4-thiadiazole.

F and F' are each a cyano group, an ester group such as ethoxy carbonyl, methoxycarbonyl, etc., an acyl group, a carbamoyl group, or an alkylsulfonyl group such as ethylsulfonyl, methylsulfonyl, etc. Examples of useful nuclei for $E_4$ include a 2-thio-2,4-oxazolidinedione nucleus (i.e., those of the 2-thio-2,4-(3H,5H)-oxaazolidinone series) (e.g., 3-ethyl-2-thio-2,4 oxazolidinedione, 3-(2-sulfoethyl)-2-thio-2,4 oxazolidinedione, 3-(4-sulfobutyl)-2-thio-2,4 oxazolidinedione, 3-(3-carboxypropyl)-2-thio-2,4 oxazolidinedione, etc.; a thianaphthenone nucleus (e.g., 2-(2H)-thianaphthenone, etc.), a 2-thio-2,5-thiazolidinedione nucleus (i.e., the 2-thio-2,5-(3H,4H)-thiazoledeione series) (e.g., 3-ethyl-2-thio-2,5-thiazolidinedione, etc.); a 2,4-thiazolidinedione nucleus (e.g., 2,4-thiazolidinedione, 3-ethyl-2,4-thiazolidinedione, 3-phenyl-2,4-thiazolidinedione, 3-a-naphthyl-2,4-thiazolidinedione, etc.); a thiazolidinone nucleus (e.g., 4-thiazolidinone, 3-ethyl-4-thiazolidinone, 3-phenyl-4-thiazolidinone, 3-a-naphthyl-4-thiazolidinone, etc.); a 2-thiazolin-4-one series (e.g., 2-ethylmercapto-2-thiazolin-4-one, 2-alkylphenyamino-2-thiazolin-4-one, 2-diphenylamino-2-thiazolin-4-one, etc.) a 2-imino-4-oxazolidinone (i.e., pseudohydantoin) series (e.g., 2,4-imidazolidinedione (hydantoin) series (e.g., 2,4-imidazolidinedione, 3-ethyl-2,4-imidazolidinedione, 3-phenyl-2,4-imidazolidinedione, 3-a-naphthyl-2,4-imidazolidinedione, 1,3-diethyl-2,4-imidazolidinedione, 1-ethyl-3-phenyl-2,4-imidazolidinedione, 1-ethyl-2-a-naphthyl-2,4-imidazolidinedione, 1,3-diphenyl-2,4-imidazolidinedione, etc.); a 2-thio-2,4-imidazolidinedione (i.e., 2-thiohydantoin) nucleus (e.g., 2-thio-2,4-imidazolidinedione, 3-ethyl-2-thio-2,4-imidazolidinedione, 3-(2-carboxyethyl)-2-thio-2,4-imidazolidinedione, 3-phenyl-2-thio-2,4-imidazolidinedione, 1,3-diethyl-2-thio-2,4-imidazolidinedione, 1-ethyl-3-phenyl-2-thio-2,4-imidazolidinedione, 1-ethyl-3-naphthyl-2-thio-2,4-imidazolidinedione, 1,3-diphenyl-2-thio-2,4-imidazolidinedione, etc.); a 2-imidazolin-5-one nucleus.

$G_2$ represents an amino group (e.g., primary amino, anilino), or an aryl group (e.g., phenyl, naphthyl, dialkylaminophenyl, tolyl, chlorophenyl, nitrophenyl).

According to the formulas D1–D5, each J represents a methine group. Examples of substituents for the methine groups include alkyl (preferably of from 1 to 6 carbon atoms, e.g., methyl, ethyl, etc.) and aryl (e.g., phenyl). Additionally, substituents on the methine groups may form bridged linkages.

$W_2$ represents a counterion as necessary to balance the charge of the sensitizing dye. Such counterions include cations and anions for example sodium, potassium, triethylammonium, tetramethylguamidinium, diisopropylammonium and tetrabutylammonium, chloride, bromide, iodide, para-toluene sulfonate and the like.

$D_1$ and $D_2$ are each independently aryl groups (preferably of 6 to 15 carbon atoms), or more preferably, alkyl groups (preferably of from 1 to 6 carbon atoms). Examples of aryl include phenyl, tolyl, p-chlorophenyl, and p-methoxyphenyl. Examples of alkyl include methyl, ethyl, propyl, isopropyl, butyl, hexyl, cyclohexyl, decyl, dodecyl, etc., and substituted alkyl groups (preferably a substituted lower alkyl containing from 1 to 6 carbon atoms), such as a hydroxyalkyl group, e.g., 2-hydroxyethyl, 4-hydroxybutyl, etc., a carboxyalkyl group, e.g., 2-carboxyethyl, 4-carboxybutyl, etc., a sulfoalkyl group, e.g., 2-sulfoethyl, 3-sulfobutyl, 4-sulfobutyl, etc., a sulfatoalkyl group, etc., an acyloxyalkyl group, e.g., 2-acetoxyethyl, 3-acetoxypropyl, 4-butyroxybutyl, etc., an alkoxycarbonylalkyl group, e.g., 2-methoxycarbonlyethyl, 4-ethoxycarbonylbutyl, etc.,or an aralkyl group, e.g., benzyl, phenethyl, etc.

According to a different embodiment, the photobleachable dye useful in the composition of the invention is an oxonol dye. Oxonol dyes can be a methine oxonol dye having the following formula:

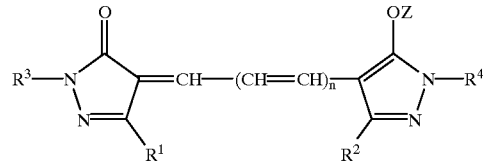

wherein n is 0, 1, or 2; $R^1$, $R^2$, $R^3$, and $R^4$ are the same or different alkyl or aryl groups, one or more of $R^1$, $R^2$, $R^3$, and $R^4$ contains carboxy substituent —$CO_2Z$, wherein $Z^+$ is a statistical mixture of hydrogen ($H^+$) and alkali or tetraalkylammonium cations ($M^+$) such that $Z^+=xH^++(1-x)M^+$, where x is a decimal ranging from about 0.33 to about 0.95. These dyes have been disclosed in details in U.S. Pat. No. 5,274,109, incorporated therein by reference.

Other oxonols useful in the present invention can be any oxonol dyes disclosed in U.S. Pat. Nos. 4,877,721, 5,674,669, EP 740,200, EP 549,486, EP 246,553, incorporated therein by reference.

The photobleachable dyes can also be a photographic filter dye of the structure

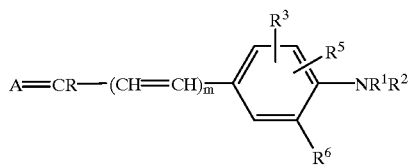

wherein A represents a nucleus having a carboxyphenyl or sulfonamidophenyl substituent selected from the group consisting of 2-pryazolin-5-ones free of any substituent bonded thereto through a carboxyl group, rhodanines, hydantoins, 2-thiohydantoins, 4-thiohydantoins, 2,4-oxazolidindiones, 2-thio-2,4-oxazolidindiones, isoxazolinones, barbiturics, 2-thiobarbiturics, and indandiones, R represent hydrogen, substituted or unsubstituted alkyl of 1 to 4 carbon atoms, or benzyl, $R^1$ and $R^2$ each independently represents substituted or unsubstituted alkyl or aryl, or taken together with $R^5$, $R^6$, N and the carbon atoms to which they are attached, represent the atoms needed to complete a julolydyl ring, $R^3$ represents H, or substituted or unsubstituted alkyl or aryl, $R^5$ and $R^6$ each independently represents H, or $R^1$ taken together with $R^1$, or $R^6$ taken together with $R^2$, represent the atoms necessary to complete a carbocyclic ring such as tetrahydroquinoyl, and m is 0 or 1. These filter dyes have been disclosed in U.S. Pat. No. 4,857,446, incorporated therein by reference.

Bleachable dyes can be azomethine dyes as disclosed in U.S. Pat. No. 5,177,052, or U.S. Pat. No. 5,871,890, incorporated therein by reference.

The photobleachable dyes useful in the composition of the present invention can also be is squarilium dyes. The squarilium can have the following formula:

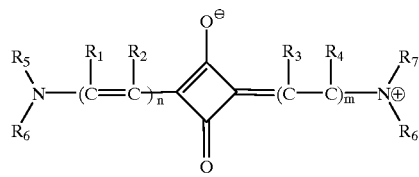

wherein: $R_1$, $R_2$, $R_3$ and $R_4$ each independently represents hydrogen, hydroxy, halogen, cyano, alkoxy, aryloxy, acyloxy, aryloxycarbonyl, alkoxycarbonyl, sulfonyl, carbamoyl, acyl, acylamido, alkylamino, arylamino or a substituted or unsubstituted alkyl, aryl or hetaryl group; or any of said $R_1$, $R_2$, $R_3$ or $R_4$ groups may be combined with $R_5$, $R_6$, $R_7$ or $R_8$ or with each other to form a 5 to 7-membered substituted or unsubstituted carbocyclic or heterocyclic ring; $R_5$, $R_6$, $R_7$ and $R_8$ each independently represents hydrogen, a substituted or unsubstituted alkyl or cycloalkyl group having from 1 to about 6 carbon atoms or an aryl or hetaryl group having from about 5 to about 10 atoms; or $R_5$ and $R_6$ or $R_7$ and $R_8$ may be joined together to form a 5 to 7-membered substituted or unsubstituted nitrogen-containing heterocyclic ring; and n and m are each independently 1 to 4. These dyes have been disclosed in details in U.S. Pat. No. 4,942,141, incorporated therein by reference.

Examples of bleachable dyes useful in the invention are:

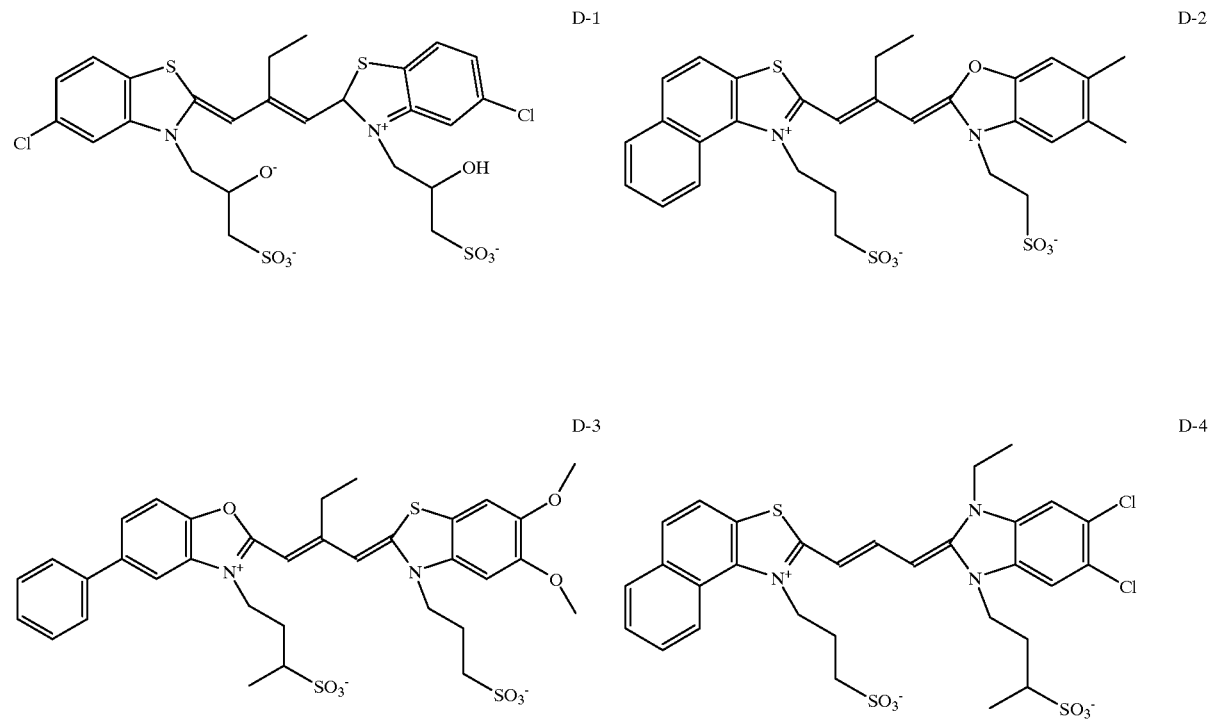

-continued
D-5
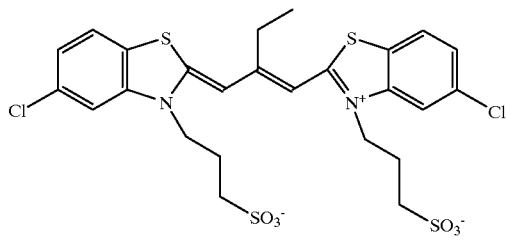
D-6
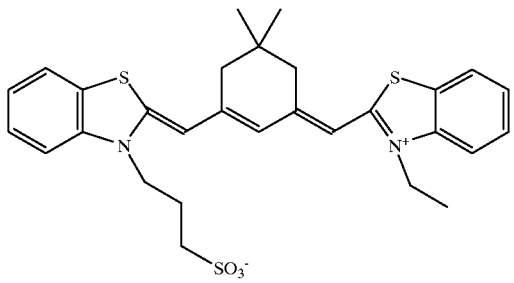
D-7
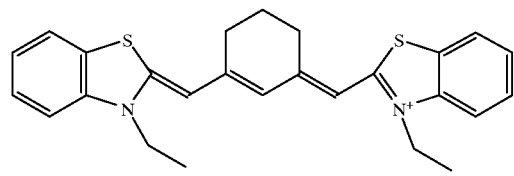
D-8
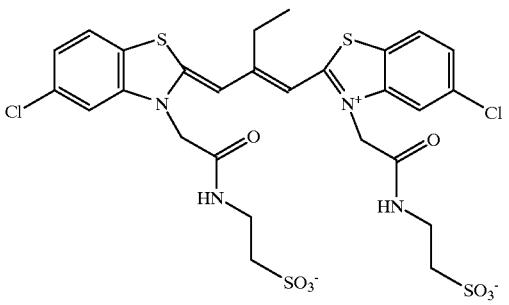
D-9
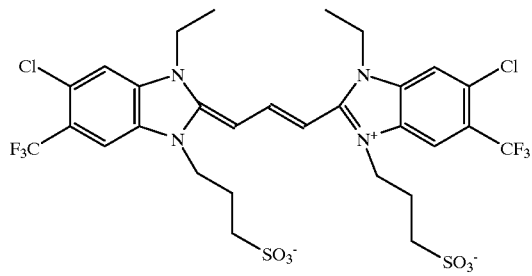
D-10
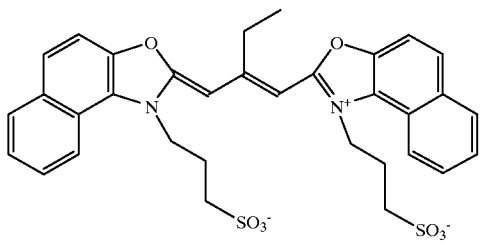
D-11
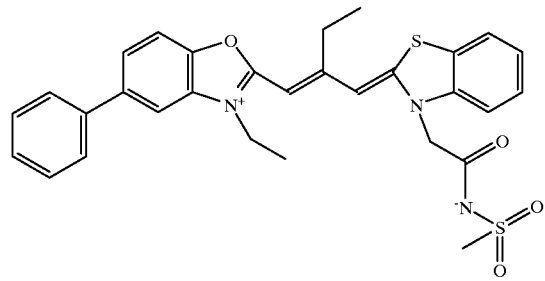
D-12
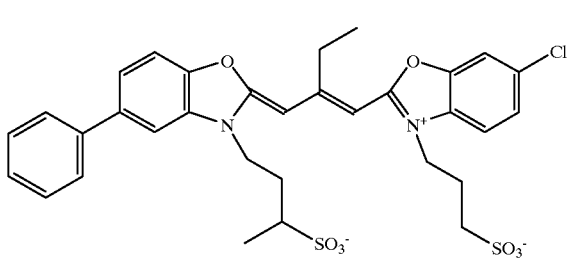
D-13
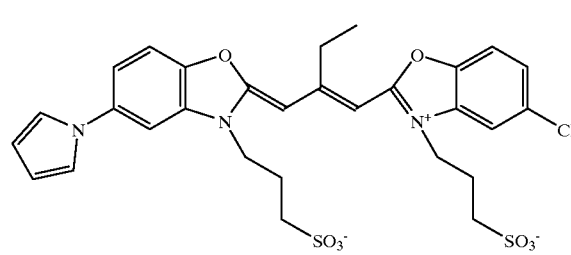
D-14
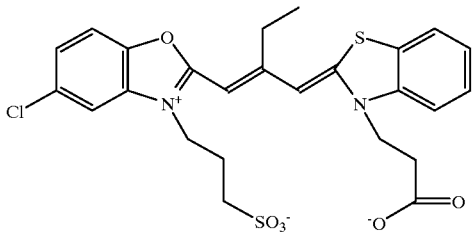

-continued
D-15
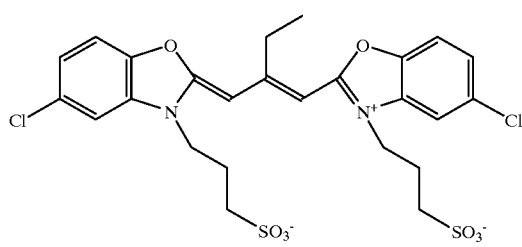
D-16
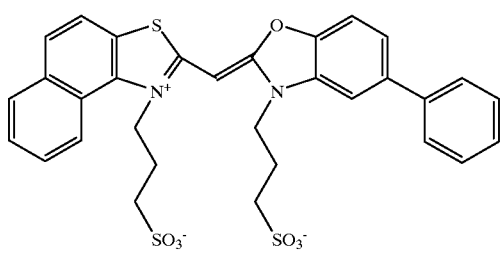
D-17
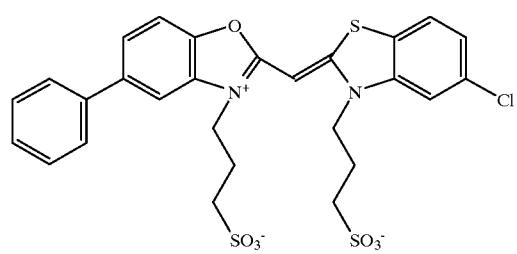
D-18
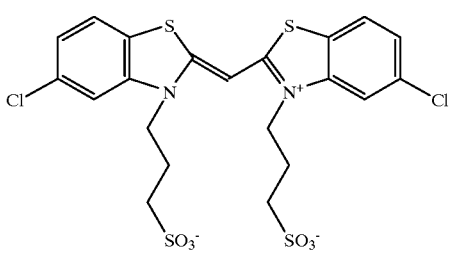
D-19
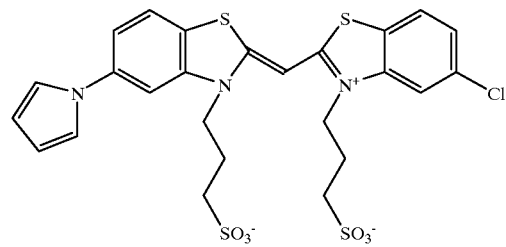
D-20
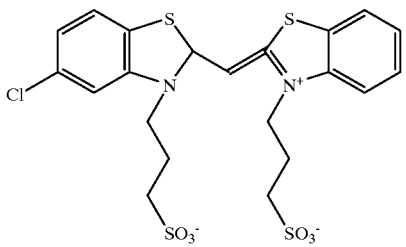
D-21
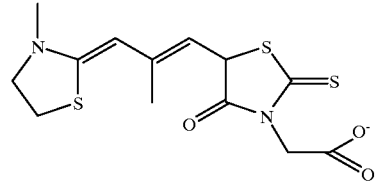
D-22
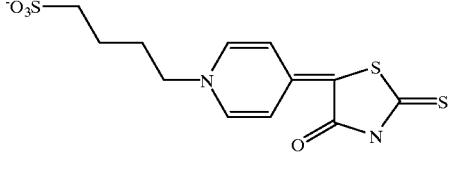
D-23
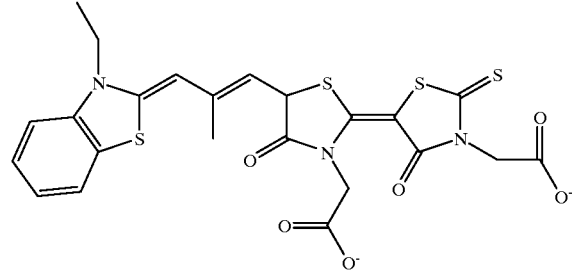
D-24
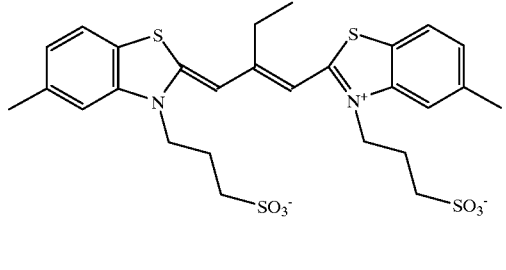
D-25
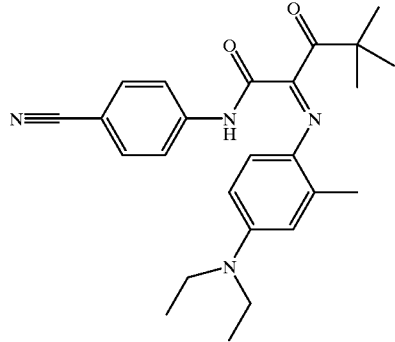

-continued
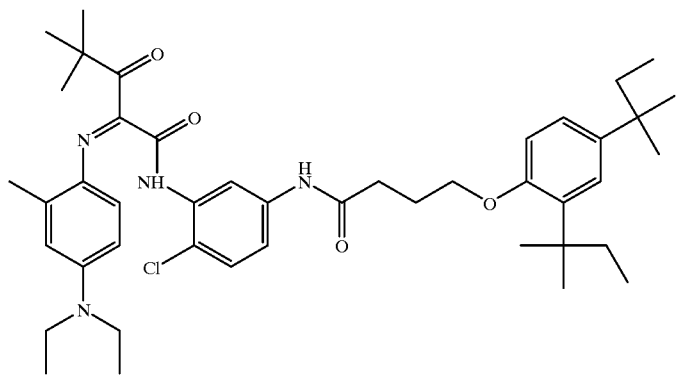
D-26
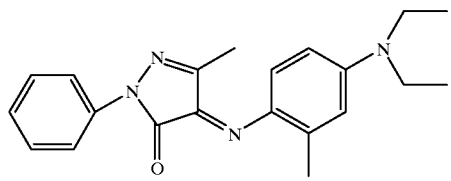
D-27
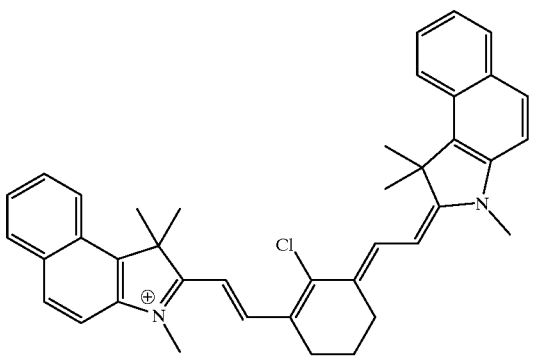
D-28
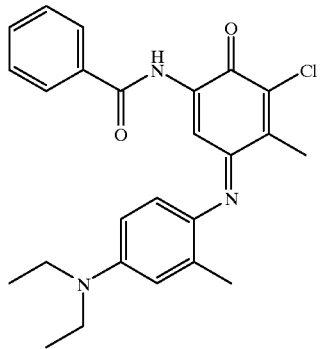
D-29
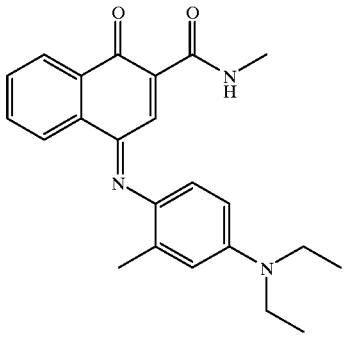
D-30
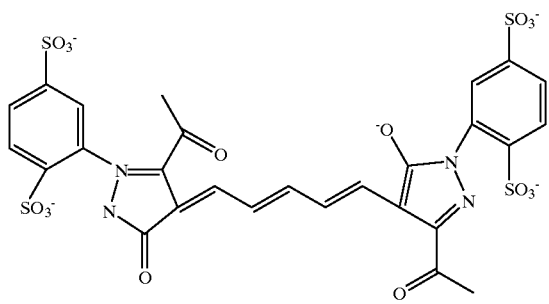
D-31

-continued
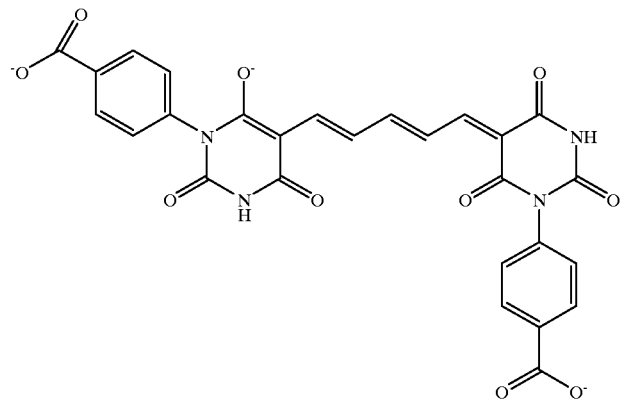
D-32
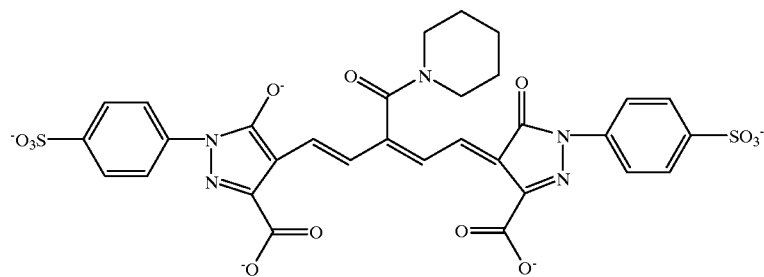
D-33
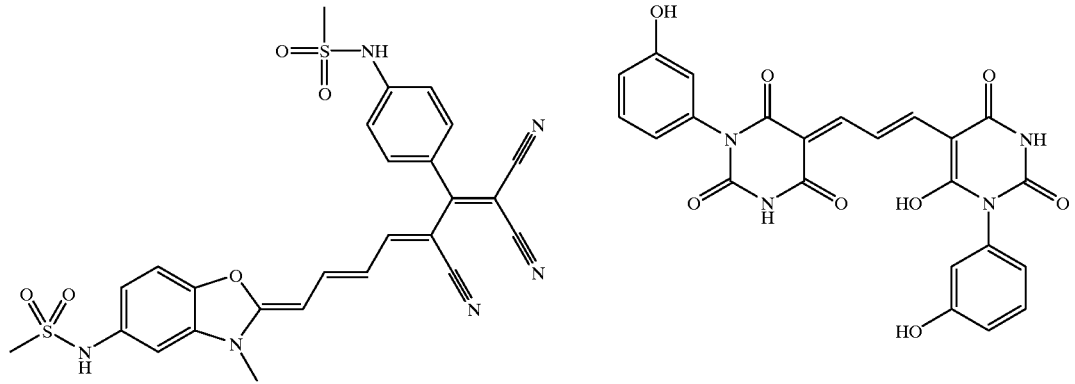
D-34
D-35
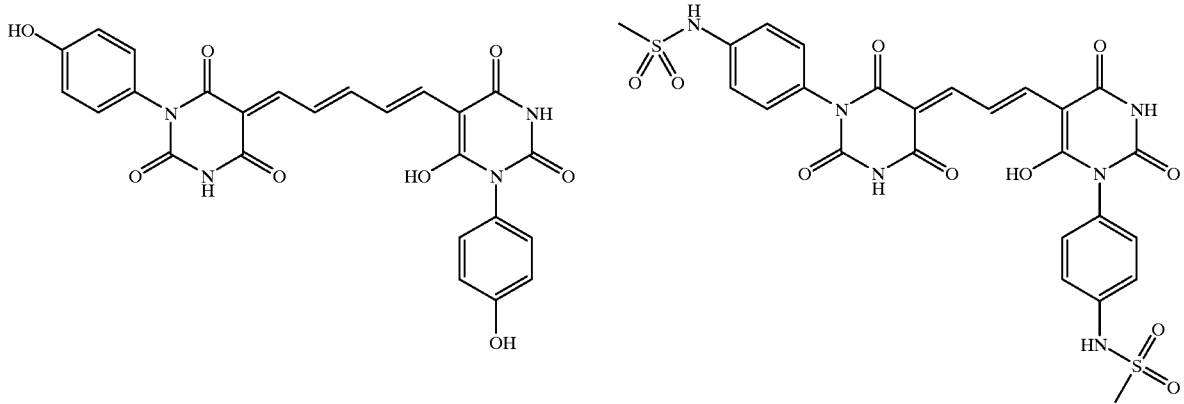
D-36
D-37

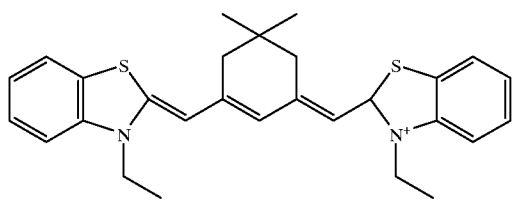
D-39
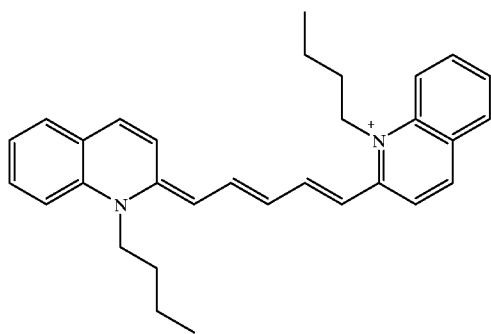
D-40
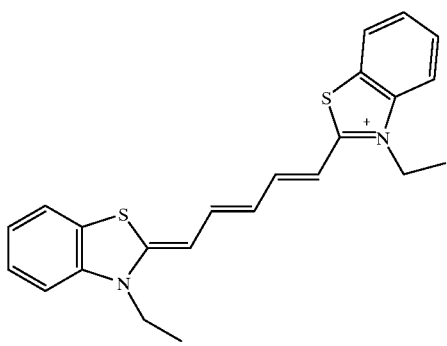
D-41
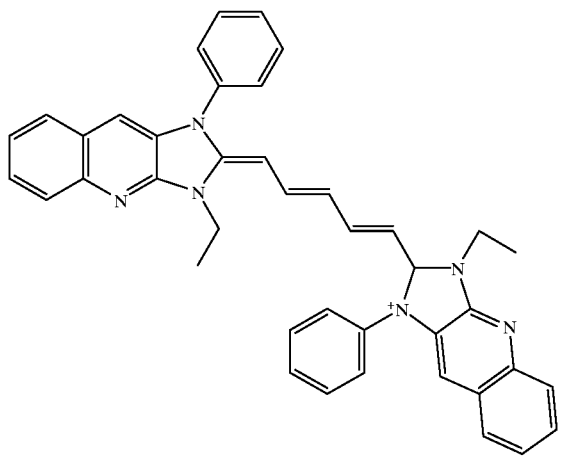
D-42
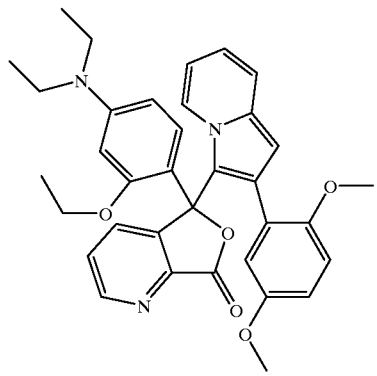
D-43
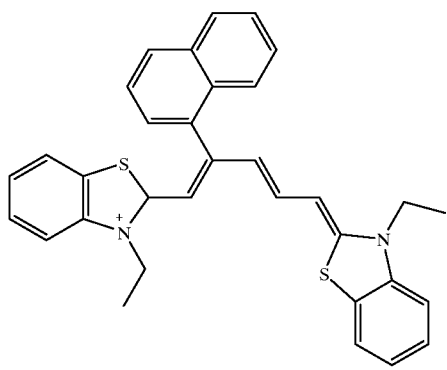
D-44
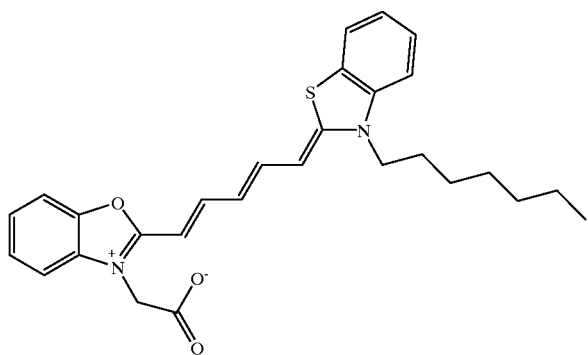
D-45

D-46
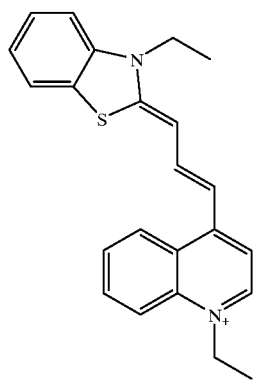
D-47
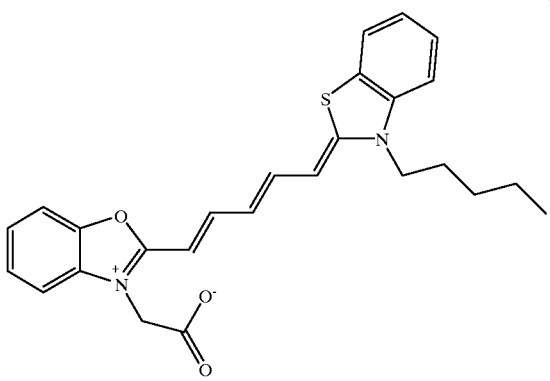
D-48
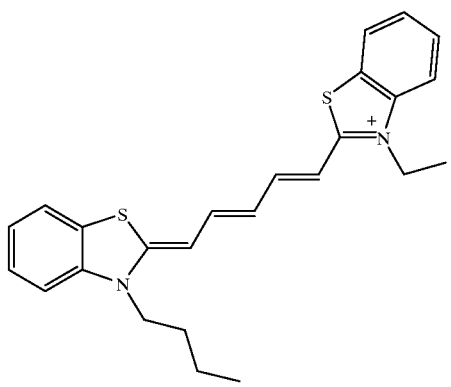
D-49
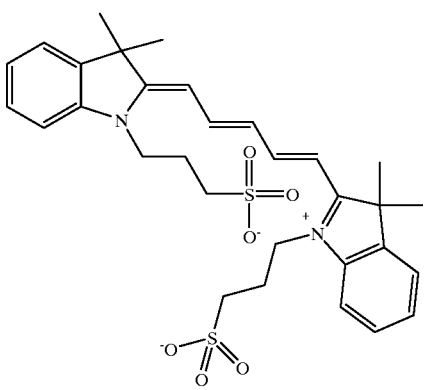
D-50
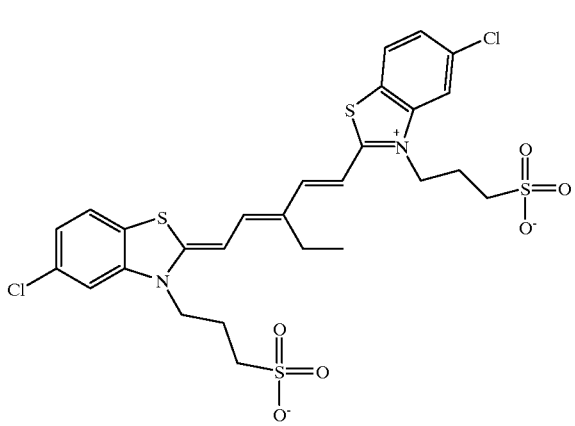
D-51
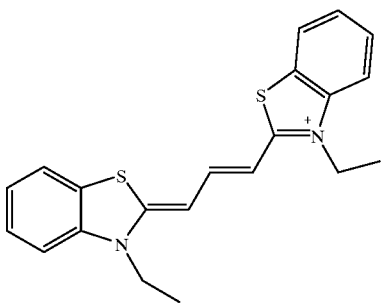
D-52
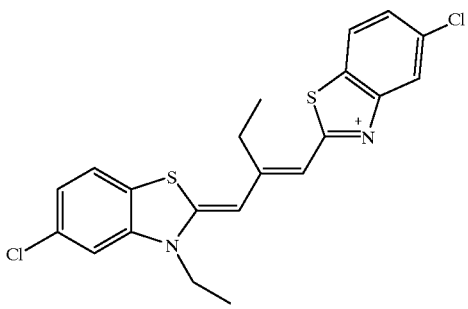
D-53
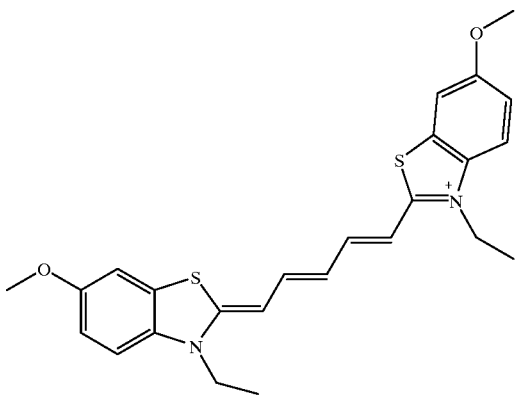

-continued
D-54
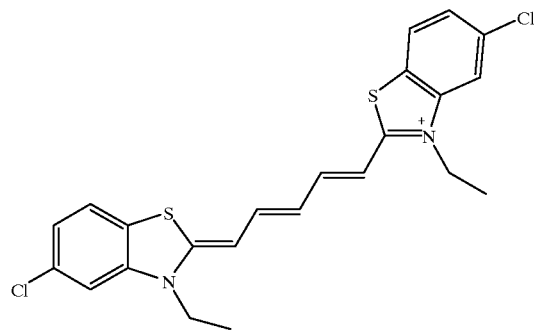
D-55
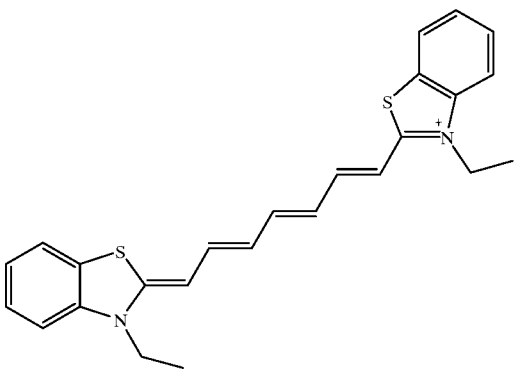
D-56
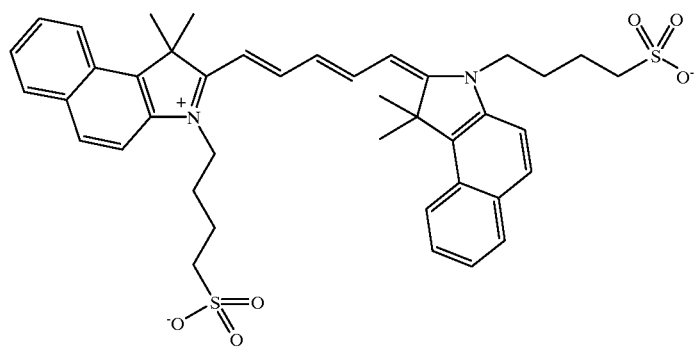
D-57
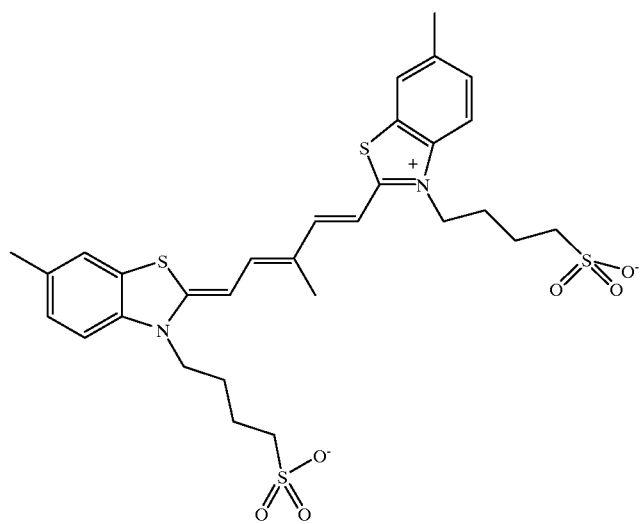

-continued
D-58
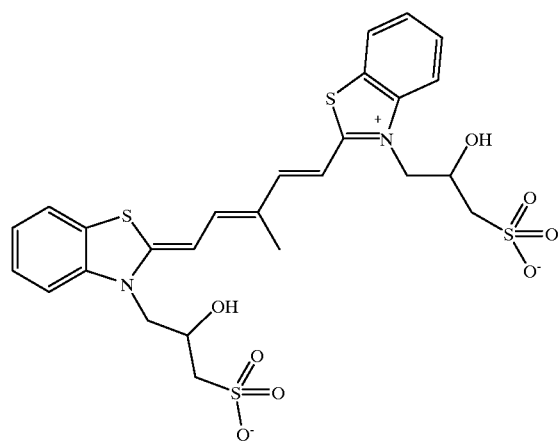
D-59
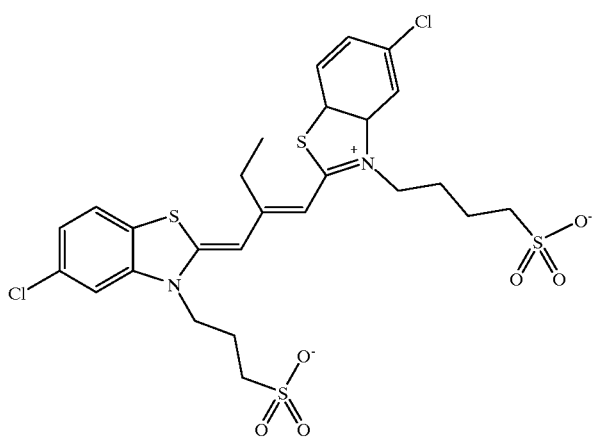
D-60
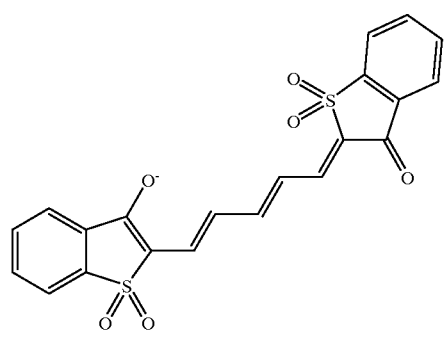
D-61
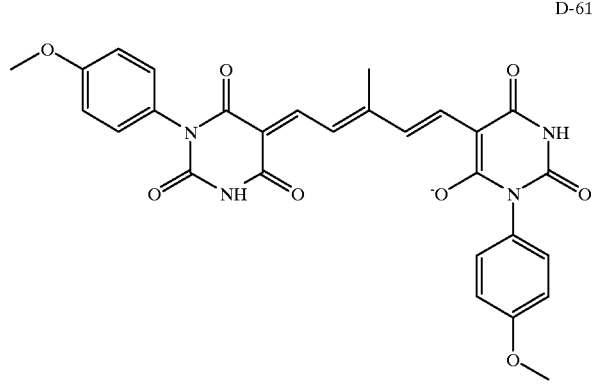
D-62
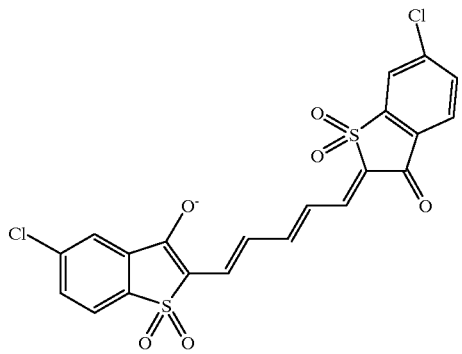
D-63
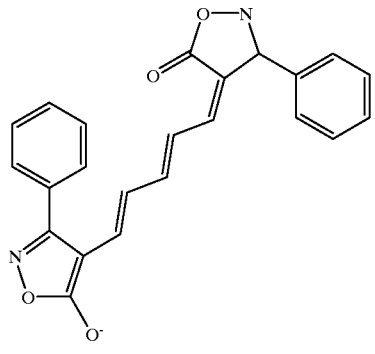
D-64
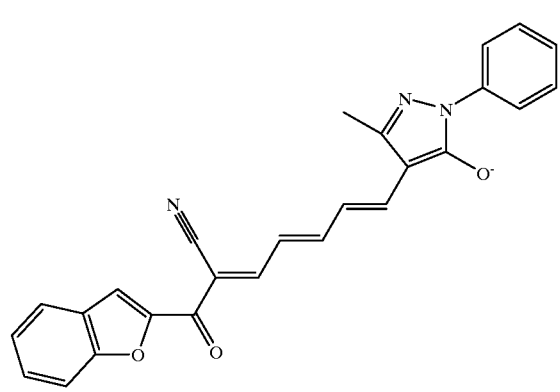
D-65
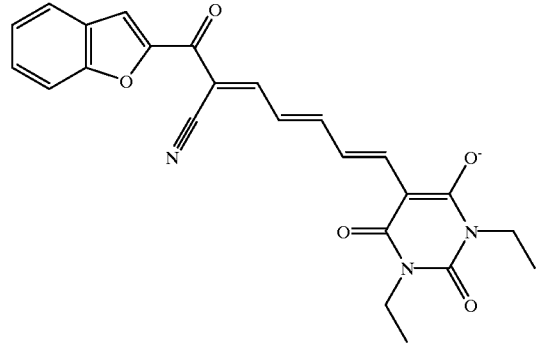

-continued
D-66
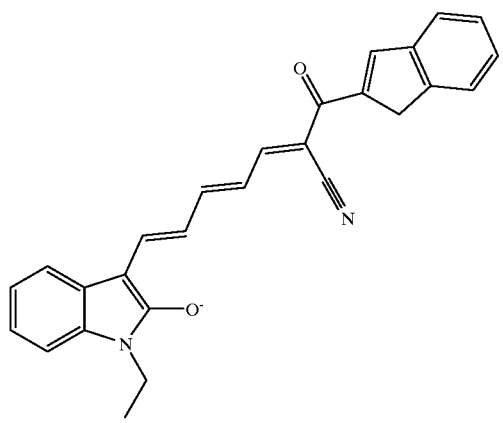
D-67
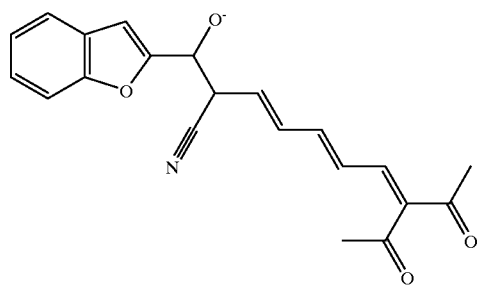
D-68
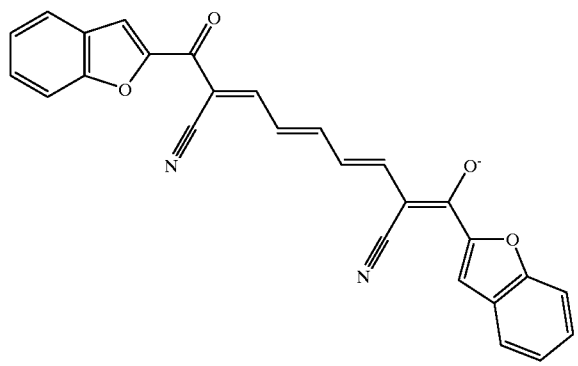
D-69
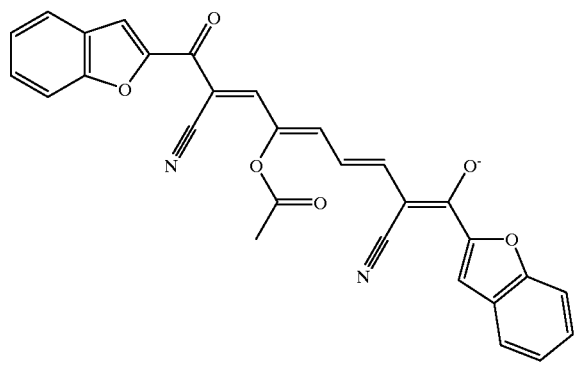
D-70
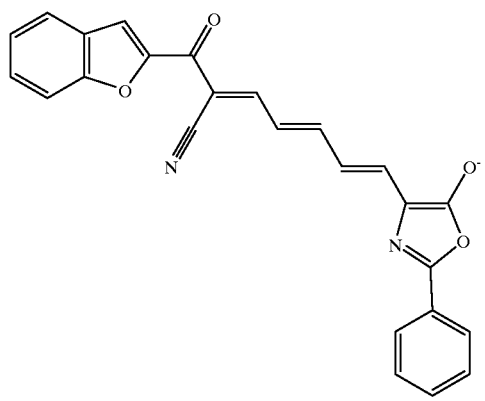
D-71
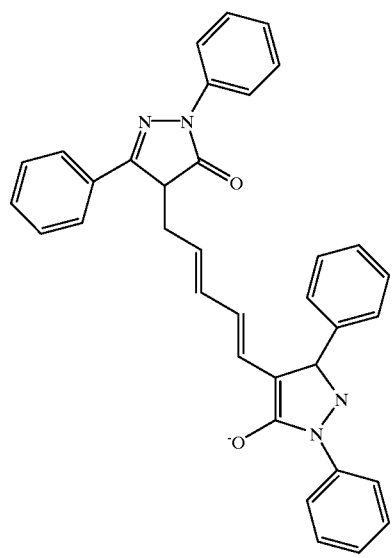

-continued
D-72
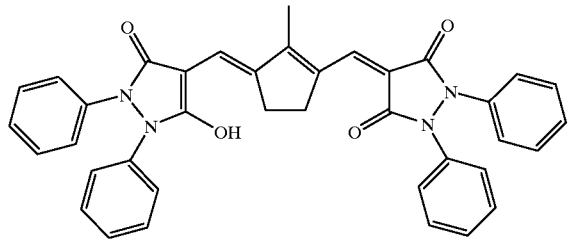
D-73
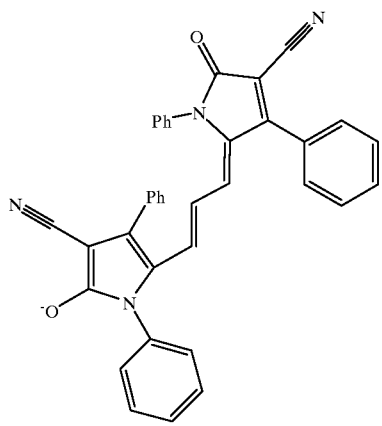
D-74
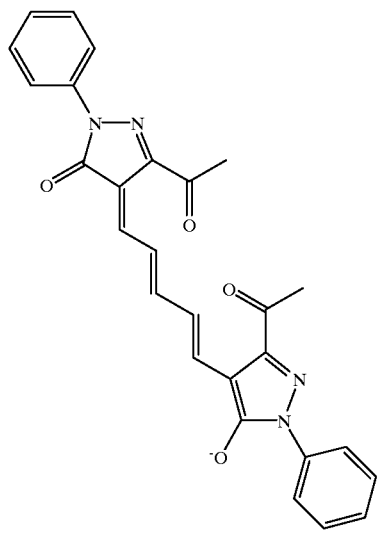
D-75
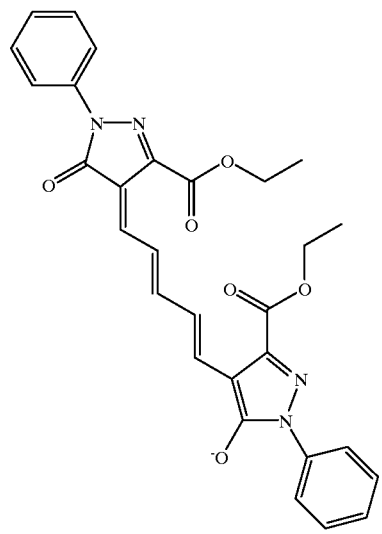
D-76
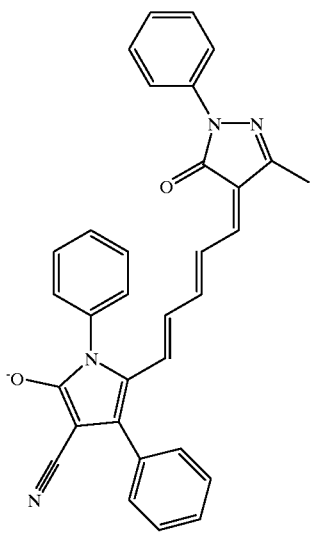
D-77
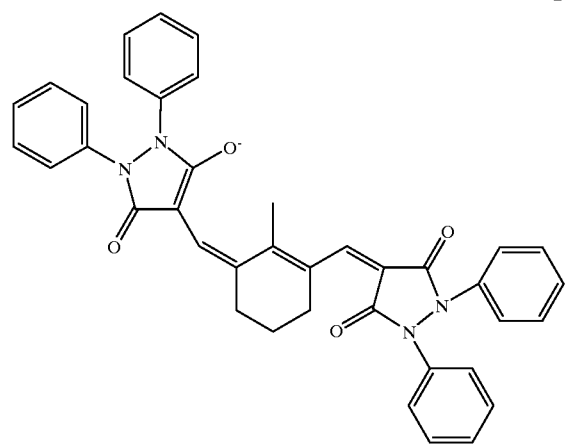

D-78
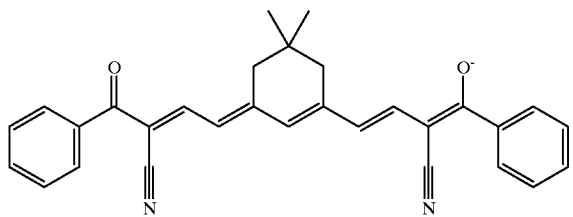
D-83
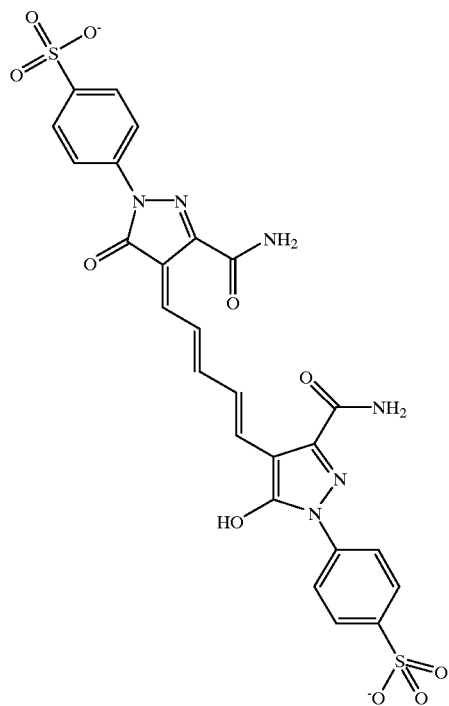
D-84
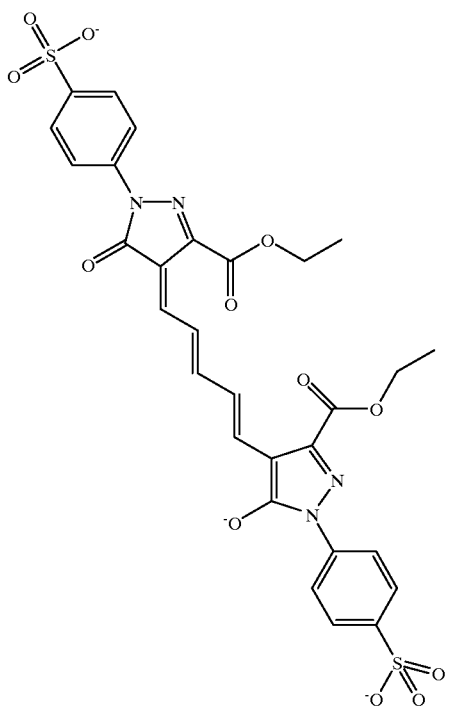
D-85
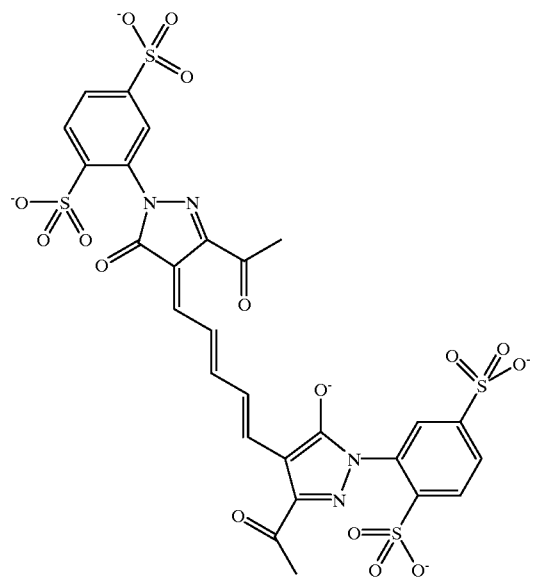

-continued
D-86
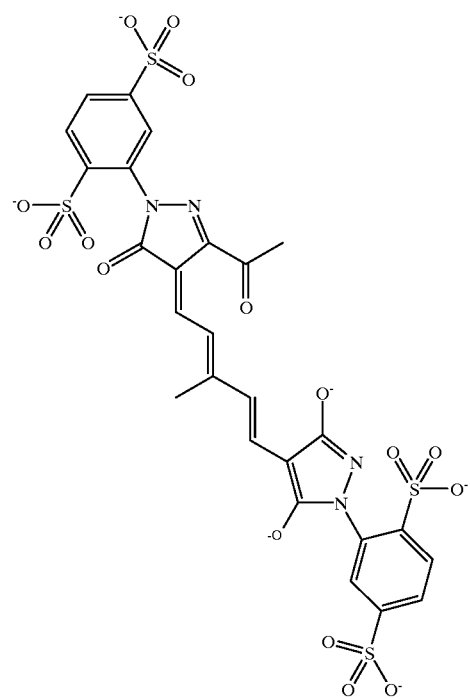
D-87
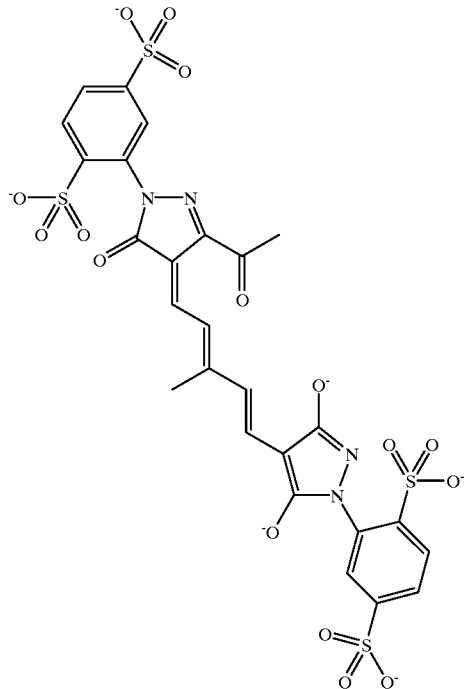
D-88
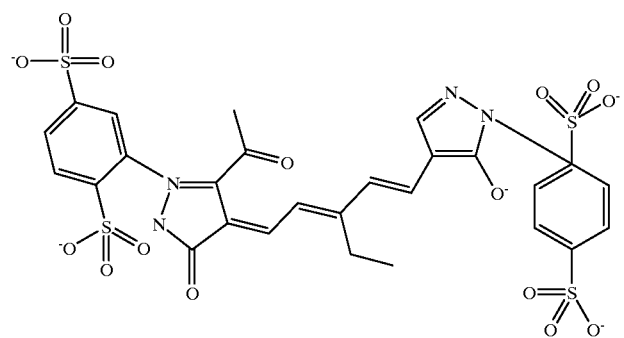
D-89
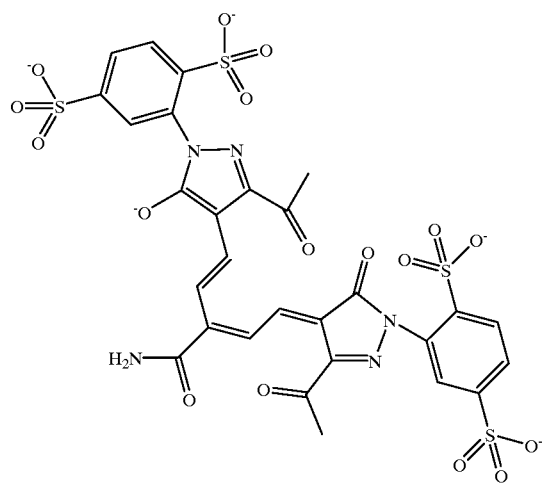
D-90
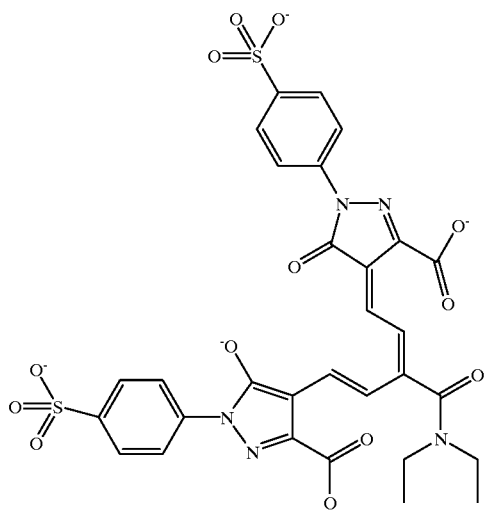

-continued
D-91
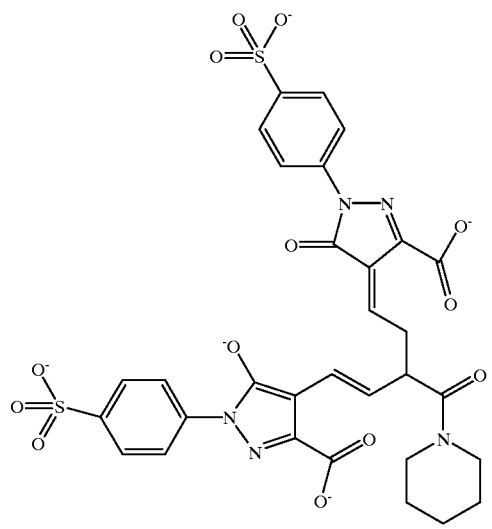
D-92
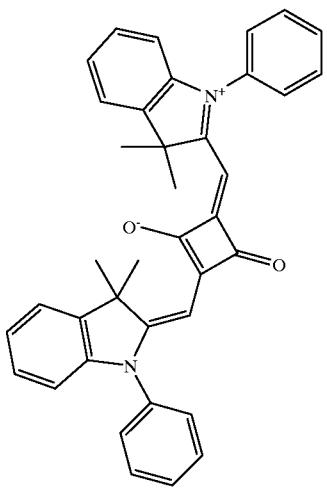
D-93
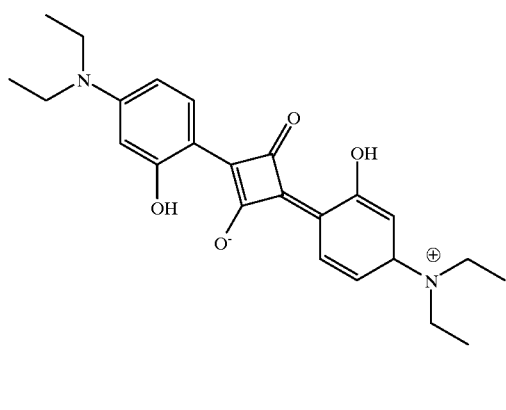
D-94
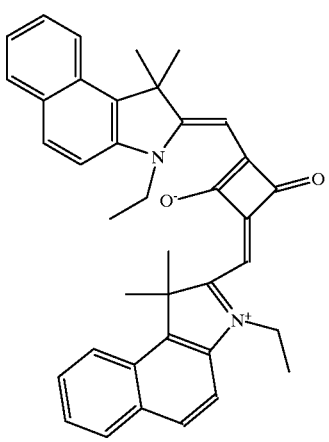
D-95
D-96
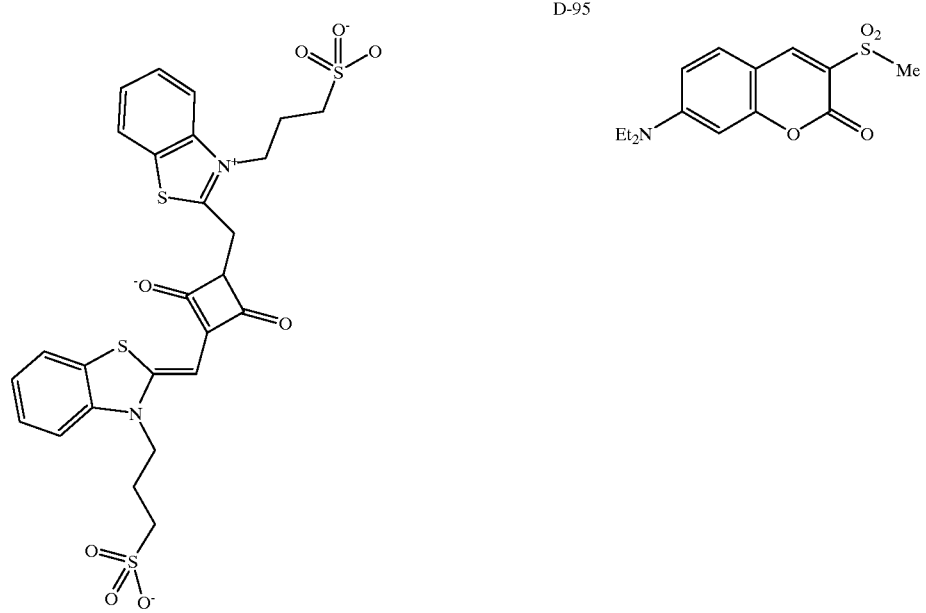

-continued
D-97 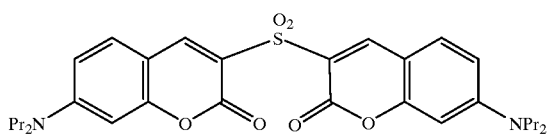
D-98 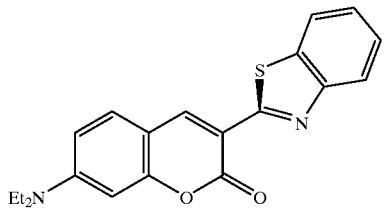
D-99 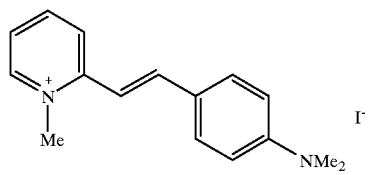
D-100 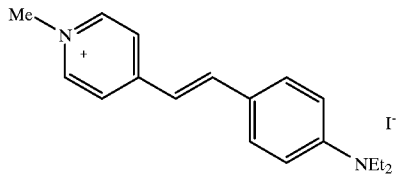
D-101 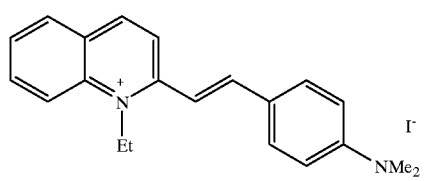
D-102 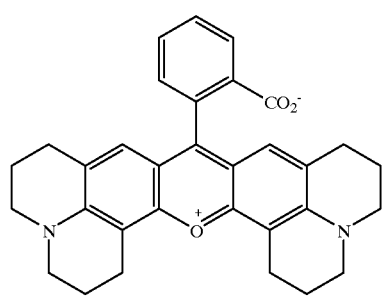
D-103 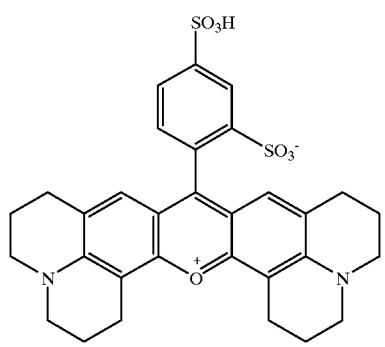
D-104 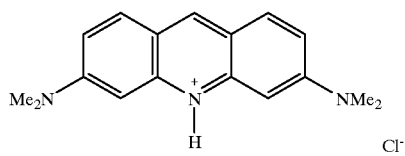
D-105 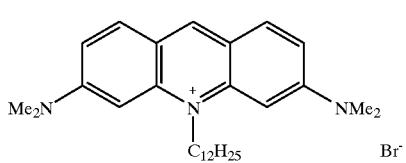
D-106 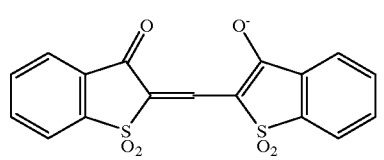
D-107 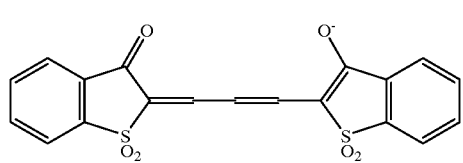
D-108 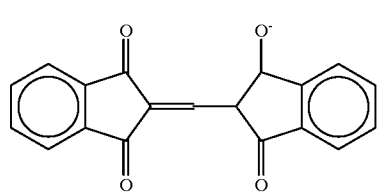
The composition of the invention can further comprise additional additives such as plasticizers, solvents, or binders. According to a specific embodiment, the composition of the invention further comprises a polymeric binder such as a polyacrylate, polymethacrylate, poly(acrylate co methacrylate) or a mixture thereof.

The photographic elements useful in the present invention can be any known photographic elements such as black and white elements, single color elements or multicolor elements. Conventionally multicolor elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like. All of these can be coated on a support that can be transparent or reflective (for example, a paper support).

The composition of the invention can be contained in any of the layers of the photographic element. According to one embodiment, the element of the invention is a photothermographic element comprising conventionally a support, preferably a transparent support, having thereon at least one photosensitive layer and a antihalation layer. In the photothermographic element of the invention, the photosensitive layer can be a silver photosensitive layer or a non-silver photosensitive layer. Non photosensitive layer can be for example a layer containing a diazo compound. According to a specific embodiment, the composition containing the N-oxyazinium is incorporated in a non image-forming layer of the photographic element of the invention, preferably in an antihalation layer.

Photographic elements comprising the composition of the invention can be processed in any of a number of well-known photographic processes utilizing any of a number of well-known processing compositions, described, for example, in T. H. James, editor, *The Theory of the Photographic Process,* 4th Edition, Macmillan, N.Y. 1977. In the case of processing a negative working element, the element is treated with a color developer (that is one which will form the colored image dyes with the color couplers), and then with a oxidizer and a solvent to remove silver and silver halide. In the case of processing a reversal color element, the element is first treated with a black and white developer (that is, a developer which does not form colored dyes with the coupler compounds) followed by a treatment to fog silver halide (usually chemical fogging or light fogging), followed by treatment with a color developer. Preferred color developing agents are p-phenylenediamines. Development is followed by bleach-fixing, to remove silver or silver halide, washing and drying.

In the method of the invention, the photobleaching can be carried out by photoexcitation of the photobleachable dye (i.e., visible to infrared light, depending on the absorption range of the dye) or by photoexcitation of the N-oxyazinium (mostly ultraviolet light). The bleaching reaction is believed to occur as a result of reaction of an alkoxy radical that results from cleavage of the N—O bond of the N-oxyazinium compound.

In the following reaction, the successive reactions are disclosed from a pyridinium compound as N-oxyazinium compound, however it should be understood that the useful compound can be any N-oxyazinium compounds useful in the scope of the invention.

In reactions induced by photoexcitation of a dye, it is believed that the excited dye (dye*) transfers an electron to the N-oxyazinium compound to yield an oxidized dye (a dye radical cation, dye$^{\cdot +}$) and a reduced N-oxyazinium compound (the radical, A$^{\cdot}$). The alkoxy radical (A$^{\cdot}$) fragments to give an oxy radical ($^{\cdot}OR_1$) and a nitrogen heterocycle (A). Reaction of the oxy radical with the dye, or with the oxidized dye (dye$^{\cdot +}$), leads to a colorless compound or a compound less colored than the dye thus providing a bleached compound.

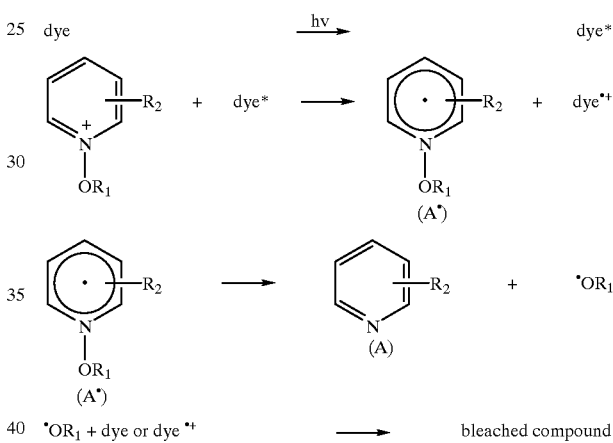

The feasibility of electron transfer from an excited dye to an N-oxyazinium compound depends on the energetics of the reaction. The reaction energetics are determined by the relative reduction potentials of the photobleachable dye and the N-oxyazinium compound. According to a preferred embodiment, the reduction potential of the N-oxyazinium compound is less negative than that of the photobleachable dye. However the reaction will still take place, although with a somewhat smaller rate constant, if the reduction potential of the N-oxyazinium compound is equal to or is slightly (ca. 0.1 V) more negative than that of the dye to be bleached.

For spectral sensitization of silver halide to occur efficiently using a sensitizing dye, the dye has to have a reduction potential which is either equal to or is more negative than ca −0.9 V, vs. SCE (saturated calomel electrode). Thus, in this embodiment, any N-oxyazinium compound with a reduction potential less negative than ca. −1.2 V would react with all sensitizing dyes.

For sensitizing dyes that have reduction potentials that are more negative than −0.9 V, the range of the reduction potentials of the N-oxyazinium compounds can be extended in accordance with the general requirement mentioned above.

The reduction potential of the N-oxyazinium compounds can be measured by conventional electrochemical techniques. Alternatively, it can be estimated from the reduction potentials of the corresponding N-alkylazinium compounds that are reported in the literature, the reduction potential of N-oxyazinium compound being always less negative than the reduction potential of the corresponding N-alkylazinium compound. The N-oxyazinium compounds listed above have reduction potentials of −0.9 V or less negative.

As mentioned above, to function as sensitizing dyes, these usually have reduction potentials of ca. −0.9 V or more negative. Thus the energetic requirements mentioned above are met for any dye that is capable of sensitizing silver halide.

It is also believed that reactions via excitation of the N-oxyazinium compounds proceed via fragmentation of the N—O bond of the photoexcited N-oxyazinium compound to yield the radical cation of the nitrogen heterocycle ($A^{\cdot+}$) and an oxy radical ($^{\cdot OR}_1$). The radical cation ($A^{\cdot+}$) can accept an electron from a dye to yield the nitrogen heterocycle (A) and the oxidized dye (a dye radical cation, $dye^{\cdot+}$). Thus, the same intermediates are ultimately formed ($^{\cdot OR}_1$ and $dye^{\cdot+}$) whether the reactions are initiated by dye excitation or by excitation of the N-oxyazinium compounds.

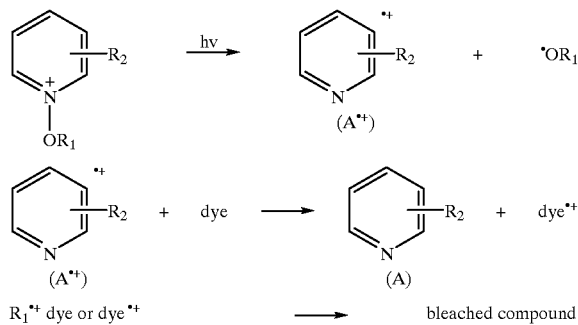

In the other embodiment of the invention the N-oxyazinium salt can be photochemically excited, where bond cleavage yielding an oxy radical and the radical cation of the parent compound as mentioned above. It was found that this excitation mode could also lead to bleaching of the dyes. The energetic requirements mentioned above for reactions initiated by the photoexcited dye do not apply to the reactions initiated by photoexcitation of the N-oxyazinium compound. The latter reactions proceed via N—O bond cleavage of the N-oxyazinium compound. The energetics of this reaction depend on the excitation energy of the N-oxyazinium compound and the N—O bond dissociation energy. N-oxyazinium compounds with first absorption maxima in the UV range or around 400 nm have excitation energies far exceeding the energy required to break the N—O bond.

In the method of the present invention, the exposed and processed photographic element is then exposed to radiation. Radiations that can be used are any radiation capable of producing the photobleaching of the dye. Radiations are selected according to the nature of the dye and for the N-oxyazinium compound. The method of the invention can be accomplished by a number of light sources. These include ambient room light from a fluorescent or incandescent lamps, from flash light, mercury or xenon light sources. The UV light may be filtered out by appropriate filters for selective exposure of the dyes, or unfiltered light may be used to excite both thedyes and the N-oxyazinium compounds. Alternatively, mostly UV light sources such as phosphor-coated low-pressure mercury lamps (300 to 350 nm) could be used. The exposure time varies from a few milliseconds when flash lamps are used to several tens of seconds when low intensity light sources are used.

When the composition of the invention contains a polymeric binder, it is preferred to carry out the method at a temperature higher than the glass transition of the polymeric binder present in the composition. If the glass transition temperature of the binder is above room temperature, exposure can be carried out at an elevated temperature or when lasers are used, the local temperature may rise to the desired level. Alternatively, an additive can be added to the composition to bring down the glass transition temperature of the composition. Such additives are well known in the art.

Next, a more detailed description of the invention will be made. However, it is to be understood that the present invention is not limited to the following examples.

EXAMPLES

Example 1

In the following experiments, solutions containing N-methoxy-4-phenylpyridinium tosylate and various photobleachable dyes were conducted in order to monitor the photo-bleaching efficiencies.

A methanolic solution of a dye indicated below (1.5 ml) was added to a methanolic solution of N-methoxy-4-phenylpyridinium tosylate (3.5 ml of 56 mM solution) in a clear glass vial. The concentration of the dye solution was such that the resulting mixture had an optical density of approximately 1.0 at the $\lambda_{max.}$ of the dye. The resulting mixture was shaken to allow complete mixing. The vial was placed on top of a regular Light Table (normal 40 Watt Cool White fluorescent lamp illumination) for 15 minutes.

A vial containing the dye solution and the appropriate amount of methanol but free of N-methoxy 4-phenylpyridinium was subjected to the same Light Table exposure. This was used as the control. Absorption spectrum was run for the experimental solution and the control.

The percent bleaching was calculated by comparing the optical densities of the experimental solution and the control at the $\lambda_{max}$ of the dye.

Tables 1, 2 and 3 contain the solution photo-bleaching data for the sensitizing dyes, image dyes and filter dyes.

TABLE 1

Solution Photo-bleaching Data for spectral Sensitizing Dyes

| Red Sensitizing Dyes | | Green Sensitizing Dyes | |
|---|---|---|---|
| Dye ID | % Bleach. | Dye ID | % Bleach |
| D-1 | 93 | D-9 | 97 |
| D-2 | 100 | D-10 | 93 |
| D-3 | 94 | D-11 | 83 |
| D-4 | 100 | D-12 | 93 |

TABLE 1-continued

| | | | |
|---|---|---|---|
| D-5 | 92 | D-13 | 95 |
| D-6 | 96 | D-14 | 65 |
| D-7 | 50 | D-15 | 92 |
| D-8 | 99 | | |
| D-24 | 98 | | |

| Blue Sensitizing Dyes | | Merocyanine Sensitizing Dyes | |
|---|---|---|---|
| Dye ID | % Bleach | Dye ID | % Bleach |
| D-16 | 72 | D-21 | 66 |
| D-17 | 64 | D-22 | 45 |
| D-18 | 83 | D-23 | 100 |
| D-19 | 76 | | |
| D-20 | 86 | | |

TABLE 2

Solution Photo-bleaching Data for the Image Dyes:

| Dye ID | % Bleaching |
|---|---|
| D-25 | 94 |
| D-26 | 95 |
| D-27 | 51 |
| D-29 | 96 |
| D-30 | 92 |

TABLE 3

Solution Photo-bleaching Data for Filter Dyes:

| Dye ID | % Bleaching |
|---|---|
| D-31 | 75 |
| D-32 | 100 |
| D-33 | 79 |
| D-34 | 94 |
| D-35 | 100 |
| D-36 | 100 |
| D-37 | 98 |

These data show that a large variety of dyes can be photobleached with a photobleaching solution containing N-methoxy-4-phenyl pyridinium.

Example 2

In these experiments, solutions containing as N-oxyazinium, the compounds listed in table 4 below and the sensitizing dye D-1 were conducted in order to monitor the photo-bleaching efficiencies under similar conditions of example 1.

The photo-bleaching data of each of the solutions are given in Table 4.

TABLE 4

Photo-bleaching Data for various N-oxyazinium compounds

| N-oxyazinium | Bleachings % |
|---|---|
| A-1 | 100 |
| A-2 | 99 |
| A-3 | 98 |
| A-10 | 100 |
| A-12 | 95 |
| A-13 | 100 |

TABLE 4-continued

Photo-bleaching Data for various N-oxyazinium compounds

| N-oxyazinium | Bleachings % |
|---|---|
| A-15 | 75 |
| A-16 | 100 |
| A-17 | 95 |
| A-18 | 97 |
| A-19 | 27 |
| A-20 | 40 |
| A-21 | 30 |
| A-22 | 64 |
| A-23 | 14 |
| A-24 | 52 |

Example 3

A solution containing 10 mg of the dye indicated in the following Table 5 below, 50 mg of N-methoxy-4-phenylpyridinium tetrafluoroborate, 250 mg dibutylphthalate, 1 g acetonitrile and, 9 g of a solution of poly(2-hydroxyethyl methacrylate) (Elvacite™ commercialized by DuPont, 8 wt % Elvacite/methylene chloride) was coated on a 5 mil clear Estar support. After drying, the films were exposed to a camera flash to determine bleachability of the dye layer.

The camera flash used for bleaching was a Promatic TCL 3200® with an illuminance of 428 lux and an irradiance of 3.63 watt/ $m^2$ at a distance of 1 m with a flash time of 820 $\mu$sec +/−5%.

Table 5 shows that substantial bleaching occurred with all three of the listed dyes in an Elvacite™ binder.

TABLE 5

| Dye | λmax | Dmax* | 5 Flash | 20 Flash |
|---|---|---|---|---|
| D-39 | 659 | 1.04 | 0.34 | 0.12 |
| D-40 | 710 | 1.15 | 0.88 | 0.69 |
| D-41 | 666 | 1.93 | 1.17 | 032 |

*Densities recorded at λmax of coating.

Example 4

Experiments 4A–4I were obtained from a solution containing 10 mg of the dye indicated in Table 6 below, 50 mg of N-methoxy-4-phenylpyridinium tetrafluoroborate, 250 mg dibutylphthalate, 1 g acetonitrile, and 9 g of a Butvar B-76 solution commercialized by Monsanto (8 wt %/acetone), coated on a 5 mil clear Estar support.

Experiments 4J–4N were obtained from a solution containing 15 mg of the dye indicated in Table 6 below, 50 mg of N-methoxy-4-phenylpyridinium tetrafluoroborate, 250 mg dibutylphthalate, 1 g acetonitrile, and 9 g of a Butvar B-76 solution commercialized by Monsanto (8 wt %/acetone) coated on a 5 mil clear Estar support.

Exposure to camera flash was performed as previously disclosed. Good bleaching was also observed with Butvar B-76 binder.

TABLE 6

| Exp. | Dye | λmax | Dmax* | 5/15 Flash |
|---|---|---|---|---|
| 4A | D-42 | 675 | 0.92 | 0.42 |
| 4B | D-43 | 652 | 036 | 0.02 |
| 4C | D-44 | 681 | 1.11 | 0.6 |
| 4D | D-45 | 633 | 0.22 | 0.06 |
| 4E | D-46 | 655 | 0.76 | 0.34 |
| 4F | D-47 | 634 | 0.21 | 0.11 |
| 4G | D-48 | 672 | 1.48 | 0.39 |
| 4H | D-49 | 658 | 0.06 | 0.03 |
| 4I | D-50 | 675 | 0.38 | 0.34 |
| 4J | D-51 | 5.73 | 0.24 | 0.10 (5f) |
| 4K | D-52 | 5.70 | 0.45 | 0.16 (5f) |
| 4L | D-53 | 685 | 0.69 | 0.21 (5f) |
| 4M | D-54 | 700 | 0.08 | 0.06 (15f) |
| 4N | D-55 | 3.74 | 0.06 | 0.05 (15f) |

*Densities recorded at λmax of coating
— data not available

Example 5

Experiments 5A–5B were obtained from a solution containing 10 mg dye indicated in Table 7 below, 50 mg of N-methoxy-4-phenylpyridinium tosylate, 500 mg of a glycerol solution in water (50 wt %), 1 g water, 9.5 g of a poly(vinylalcohol) PVA solution in water (6.2 wt. %), coated on a 5 mil clear Estar support.

Experiments 5C–5D were obtained from a solution containing 15 mg dye indicated in Table 7 below, 50 mg of N-methoxy-4-phenylpyridinium tetrafluoroborate, 500 mg of a glycerol solution in water (50 wt. %), 1 g water, 9.5 g of a PVA solution in water (6.2 wt. %), coated on a 5 mil clear Estar support. Bleaching was preformed as disclosed in example 3.

Exposure and processing were as disclosed in example 4.

As shown in Table 7, rapid bleaching was seen.

TABLE 7

| Exp. | Dye | λmax | Dmax* | 5 or 15-Flash |
|---|---|---|---|---|
| 5A | D-56 | 693 | 1.36 | 0.92 (5f) |
| 5B | D-57 | 673 | 1.03 | 0.23 (5f) |
| 5C | D-58 | 672 | 1.30 | 0.71 (5f) |
| 5D | D-59 | 570 | 1.30 | 0.42 (15f) |

*Densities recorded at λmax of coating

Example 6

On the backside of a clear Estar support coated with a standard photothermographic emulsion (composition shown below) sensitized to 633 nm and an overcoat layer, was coated a mixture of 11.9 mg of the antihalation dye D-92, 50 mg N-methoxy-4-phenylpyridinium tetrafluoroborate, 1 g acetonitrile, 9 g of a Butvar solution (8% acetone), 250 mg dibutylphthalate with a 5 mil knife under pan lights.

After drying, the article was exposed with an EG&G sensitometer for $10^{-3}$ sec through Wratten 29 and 47 filters and processed for 5 sec at 119° C. using a comstar processor.

The control, with no halation protection, showed blurry edges in the step tablets. The present invention shows sharp images in the red exposure areas. The cyan color of the antihalation dye was still present after processing, but could be bleached on exposure to a camera flash.

| Emulsion Layer | Coated at 6.4 cm³/ft² | Amount (g) |
|---|---|---|
| Ag behenate dispersion | 37.53 g Ag/L in 6.2% B-76 in MIBK | 871.24 |
| AgBr emulsion | 40.91 g Ag/L in 13.2% B-76 in MIBK | 163.85 |
| succinimide | 10% in 10.5% B-76 in acetone | 88.58 |
| surfactant | 10% in MIBK | 1.52 |
| monobromo | 2.5% in 10.5% B-76 in acetone | 96.30 |
| triazone | 2.5% in 10.5% B-76 in acetone | 23.27 |
| dye | 0.2% in MeOH | 134.19 |
| sulfonamido phenol | 10% in 10.5% B-76 in MIBK | 392.07 |
| palmitic acid | 10% in 10.5% B-76 in acetone | 29.40 |
| BUTVAR B-76 ® | 10.5% in MIBK | 299.28 |

MIBK: Methylisobutylketone

| Overcoat | Coated at 3.75 cm3/ft2 | Amount(g) |
|---|---|---|
| Elvanol | 6.4% in water | 629.25 |
| water | | 487.05 |
| Olin 10G ® | 10% in water (surfactant) | 15.00 |
| Tetraethyl orthosilicate | | 367.20 |
| water | | 117.55 |
| p-toluenesulfonic acid | 1 N in water | 4.90 |
| methanol | | 136.05 |
| tetraethylorthosilicate | | 141.50 |

-continued

| Overcoat | Coated at 3.75 cm3/ft2 | Amount(g) |
|---|---|---|
| monobromo | dye | triazine |

Example 7

A solution containing 10 mg of dye D-60, 20 equivalent of the N-oxyazinium compound bleaching agent indicated in the Table 8 below, 250 mg dibutylphthalate, 1 g acetonitrile, and 9 g of a solution of Elvacite™ (8 wt %) was coated on a 5 mil clear Estar support. After drying, the films were then exposed to a camera flash to determine bleachabilility of this antihalation layer according to the method disclosed in example 3.

The camera flash used for bleaching was a Promatic TCL 3200® with an illuminance of 428 lux and an irradiance of 3.63 watt/m² at a distance of 1 m with a flash time of 820 $\mu$sec+/−5%. The Hg lamp was a 200 watt high pressure, short arc Hg lamp. The exposure to the Hg lamp was 30 sec.

Table 8 shows that N-oxyazinium with phenyl substituents, allowed bleaching to proceed efficiently when subjected to 20 flashes. The methyl analog, was much less efficient. However, all three N-oxyazinium allowed complete bleaching when irradiated for 30 sec with the Hg lamp.

TABLE 8

| N-oxyazinium | Dmax* | 5 Flash | 20 Flash | Hg lamp |
|---|---|---|---|---|
| MPF | 2.27 | 0.40 | 0.01 | 0.01 |
| MPT | 2.38 | 1.38 | 0.01 | 0.01 |
| MMPT | 2.26 | 2.00 | 1.22 | 0.01 |

*Densities recorded at λmax of coating.
MPF: N-methoxy-4-phenylpyridinium tetrafluoroborate
MPT: N-methoxy-4-phenylpyridinium tosylate
MMPT: N-methoxy-4-methylpyridinium tosylate

Example 8

In these experiments, a solution containing 10 mg of dye D-60, 50 mg of N-methoxy-4-phenylpyridinium tetrafluoroborate, 250 mg dibutylphthalate, 1 g acetonitrile, and 9 g of a binder solution indicated in the following Table 9 was coated on a 5 mil clear Estar support. Bleaching was performed as previously disclosed.

Table 9 shows that all five substantially different binders allowed good photobleaching of the antihalation layer.

TABLE 9

| Binder | Tg (° C.) | Dmax* | 5 Flash | 20 Flash | Hg Lamp |
|---|---|---|---|---|---|
| Elvacite | 109 | 2.21 | 0.32 | 0.09 | 0.01 |
| Butvar | 68 | 1.53 | 0.20 | 0.01 | 0.01 |
| PMMA | 114 | 2.20 | 0.10 | 0.01 | 0.01 |
| Polycarbonate | 149 | 2.19 | 0.21 | 0.09 | 0.01 |
| CAB | 136 | 2.40 | 0.27 | 0.03 | 0.01 |

*Densities recorded at λmax of coating.
PMMA polymethylmethacrylate
CAB: Cellulose Acetate Butyrate
Tg: glass transition temperature

Example 9

A solution containing 10 mg of the dye indicated in Table 10 below, 50 mg of N-methoxy-4-phenylpyridinium tetrafluoroborate, 250 mg dibutylphthalate, 1 g acetonitrile, 9 g Elvacite™ (8 wt %) was coated on a 5 mil clear Estar support. After drying, bleaching was performed as previously disclosed.

The bleaching results are given Table 10, below.

TABLE 10

| Dye | λmax | Dmax | 5 Flash | 20 Flash |
|---|---|---|---|---|
| D-61 | 715 | 0.06 | 0.05 | 0.05 |
| D-62 | 663 | 2.34 | 0.86 | 0.12 |
| D-63 | 631 | 0.24 | 0.09 | 0.05 |
| D-64 | 660/490 | 0.40/0.53 | 0.18/0.35 | 0.07/0.21 |
| D-65 | 637 | 1.15 | 1.00 | 0.09 |
| D-66 | 660/558 | 0.20/0.23 | 0.06/0.10 | 0.04/0.08 |
| D-67 | 665/420 | 0.17/0.26 | 0.06/0.26 | 0.04/0.24 |
| D-68 | 660/560 | 0.06/0.19 | 0.02/0.09 | 0.02/0.02 |
| D-69 | 659 | 1.49 | 0.20 | 0.08 |
| D-70 | 560 | 0.27 | 0.05 | 0.03 |
| D-71 | 665/480 | 0.12/0.17 | 0.08/0.14 | 0.04/0.10 |
| D-72 | 670 | 1.45 | 1.02 | 0.04 |
| D-73 | 700 | 0.03 | 0.00 | 0.00 |
| D-74 | 681 | 2.00 | 0.11 | 0.04 |
| D-75 | 684 | 0.14 | 0.02 | 0.00 |
| D-76 | 514 | 0.48 | 0.34 | 0.20 |
| D-77 | 654 | 1.50 | 0.13 | 0.04 |
| D-78 | 477 | 1.05 | 1.02 | 0.82 |

Example 10

A solution containing 10 mg of the dye indicated in Table 11 below, 50 mg N-methoxy-4-phenylpyridinium tetrafluoroborate, 500 mg of a glycerol water solution (50%), 1 g water, 9 g of a solution PVA in water (6.1 wt %)

was coated on a 5 mil clear Estar support. After drying for 2 minutes, bleaching was performed as already disclosed. The bleaching results are given Table 11 below.

TABLE 11

| Dye | λmax | Dmax* | 5 Flash |
|---|---|---|---|
| D-83 | 663 | 0.59 | 0.15 |
| D-84 | 671 | 1.11 | 0.54 |
| D-85 | 681 | 0.47 | 0.03 |
| D-86 | 702 | 0.41 | 0.03 |
| D-87 | 702 | 0.57 | 0.05 |
| D-88 | 703 | 0.16 | 0.01 |
| D-89 | 710 | 0.20 | 0.05 |
| D-90 | 696 | 0.79 | 0.05 |
| D-91 | 689 | 0.23 | 0.08 |

Example 11

In experiments 11A and 11B, a solution containing 10 mg of the dyes as indicated in table 12, 50 mg N-methoxy-4-phenylpyridinium tetrafluoroborate, 1 g acetonitrile, 250 mg of dibutylphthalate and 9 g of a 8 wt % solution of Elvacite™ was coated on a 5 mil clear Estar support. After drying for 2 minutes, the bleaching was performed as disclosed in example 7.

In experiment 11C, the coating solution was the solution of Example 11A wherein Elvacite™ was replaced by a Butvar solution and the dye was as indicated below.

In Experiment 11D, the coated solution was a solution containing 10 mg of the dye, 56 mg N-methoxy-4-phenylpyridinium tosylate, 1 g water, 500 mg of 50% glycerol in water and 9 g of 6.1% PVA and the dye was as indicated below.

TABLE 12

| Dye | Experiment | λmax | Dmax* | Hg Lamp (30 sec) | 5 Flash |
|---|---|---|---|---|---|
| D-92 | 11A | 649 nm | 1.06 | 0.05 | — |
| D-93 | 11B | 650 nm | 2.42 | 0.53 | — |
| D-94 | 11C | 671 nm | 1.11 | — | 0.76 |
| D-95 | 11D | 669 nm | 0.36 | 0.01 | — |

— data not available

Example 12

The backside of the photothermographic element described in Example 6, was coated with a mixture of 5 mg of dye D-92, 50 mg N-methoxy-4-phenylpyridinium tetrafluoroborate, 1 g acetonitrile, 9 g (8%) solution of Elvacite™, 250 mg dibutylphthalate with a 5 mil knife under pan lights. After drying the sensitometer for $10^{-3}$ sec through a Wratten 29 and 47 filters and processed for 5 sec at 119° C.

The control with no halation protection, showed blurry edges in the step tablets. The present invention shows sharp images in the red exposure areas. The cyan color of the antihalation dye was still present after processing but could be bleached on exposure to a camera flash to go from D=0.41 to D=0.23. Residual density is due to the emulsion sensitizing dye remaining in the film.

Example 13

A solution containing D-28 and 0.12 M of N-methoxy-4-phenylpyridinium tetrafluoroborate in acetonitrile was irradiated with a xenon lamp (λ>600 nm). Upon 7.5 min. of irradiation, the optical density at 805 nm dropped from 1.6 to less than 0.10.

The invention has been described in detail with particular reference to certain preferred embodiments thereof, but it will be understood that variations and modifications can be effected within the spirit and scope of the invention.

What is claimed is:

1. An imaging element comprising a support having thereon at least one image forming layer, and at least one nonimage forming layer wherein the element further comprises a visible light sensitive photobleachable composition containing a photobleachable dye which does not contain an N-oxyazinium group and which reacts with an N-oxyazinium compound to form a bleached compound and an N-oxyazinium compound; wherein the photobleachable dye and the N-oxyazinium compound are distinct entities.

2. The element of claim 1, wherein the N-oxyazinium compound has a reduction potential less negative than −1.2 V, and comprises an N-oxy group capable of releasing an oxy radical that reacts with the photobleachable dye to produce bleached compound.

3. The element of claim 1 wherein the N-oxyazinium compound is represented by one of the following formulae:

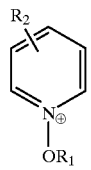

(II)

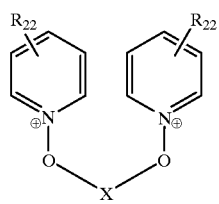

(III)

wherein $R_1$ is a n alkyl, an aryl or an acyl, $R_2$ or $R_{22}$ are independently an hydrogen atom, alkyl, aryl, heterocyclic, carboxylic, carboxylate, carbonamido, sulfonamido, nitryl, groups, —CO—$R_3$ wherein $R_3$ is an alkyl group or aryl group, or —(CH=CH)$_m$—$R_4$ group wherein $R_4$ is an aryl or heterocyclic group or $R_2$ or $R_{22}$ can form a fused ring system with the phenyl group to which they are attached; X is an alkylidene group.

4. The element of claim 1 wherein the N-oxyazinium compound is an N-alkyloxyazinium compound.

5. The element of claim 1 wherein the photobleachable dye is a filter dye or an antihalation dye.

6. The element of claim 1, wherein the photobleachable composition is in corporated in the non image-forming layer.

7. The element of claim 6, wherein the non image-forming layer containing the photobleachable dye is an halation layer.

8. The element of claim 1 wherein the element is a silver halide photographic element.

9. The element of claim 1 wherein the element is a photothermographic element.

* * * * *